United States Patent [19]

Heeres et al.

[11] 4,358,449
[45] Nov. 9, 1982

[54] 1-(1,3-DIOXOLAN-2-YLMETHYL)-1H-1,2,4-TRIAZOLES AND COMPOSITIONS

[75] Inventors: Jan Heeres, Vosselaar; Leo J. J. Backx, Arendonk; Joseph H. Mostmans, Antwerp, all of Belgium

[73] Assignee: Janssen Pharmaceutica, N.V., Beerse, Belgium

[21] Appl. No.: 351,671

[22] Filed: Feb. 15, 1980

Related U.S. Application Data

[63] Continuation of Ser. No. 1,614, Jan. 8, 1979, abandoned, which is a division of Ser. No. 853,728, Nov. 21, 1977, Pat. No. 4,144,346, which is a continuation-in-part of Ser. No. 764,263, Jan. 31, 1977, abandoned.

[51] Int. Cl.$^3$ ............... A61K 31/535; A61K 31/445; C07D 413/14

[52] U.S. Cl. .................. 424/248.58; 424/250; 424/267; 424/269; 544/132; 544/366; 546/210; 548/262

[58] Field of Search .............. 544/132, 366; 546/210; 548/262; 424/248.58, 250, 267, 269

[56] References Cited

PUBLICATIONS

Van Reef et al., *Chemical Abstracts*, vol. 85 (1976), No. P94368f.

*Primary Examiner*—Robert W. Ramsuer
*Attorney, Agent, or Firm*—Geoffrey G. Dellenbaugh

[57] ABSTRACT 1-(1,3,-Dioxolan-2-ylmethyl)-1H-imidazoles and 1H-1,2,4-triazoles useful as antifungal and antibacterial agents.

7 Claims, No Drawings

1-(1,3-DIOXOLAN-2-YLMETHYL)-1H-1,2,4-TRIAZOLES AND COMPOSITIONS

CROSS-REFERENCE TO RELATED APPLICATIONS

This is a continuation, of application Ser. No. 1,614, filed Jan. 8, 1979 now abandoned, which in turn is a division of application Ser. No. 853,728, filed Nov. 21, 1977, now Pat. No. 4,144,346, which in turn is a continuation-in-part of application Ser. No. 764,263, filed Jan. 31, 1977, now abandoned.

BACKGROUND OF THE INVENTION

In U.S. Pat. Nos. 3,575,999, 3,936,470 and Belg. Pat. No. 835,579 there are described a number of 1-(1,3-dioxolan-2-ylmethyl)-1H-imidazoles and 1H-1,2,4-triazoles having antifungal and antibacterial properties. The compounds of this invention differ from the foregoing essentially by the nature of the substituent group in the 4-position of the dioxolane moiety.

DESCRIPTION OF THE PREFERRED EMBODIMENTS

This invention is concerned with novel 1H-imidazole and 1H-1,2,4-triazole derivatives which may structurally be represented by the formula:

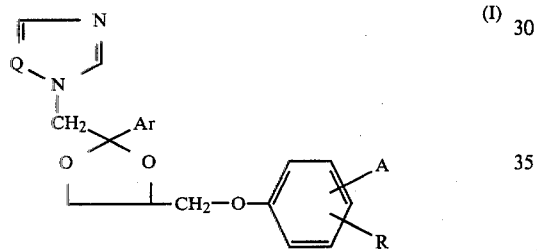

and the pharmaceutically acceptable acid addition salts and stereochemically isomeric forms thereof, wherein:
Q is a member selected from the group consisting of CH and N;
Ar is a member selected from the group consisting of phenyl and substituted phenyl, said substituted phenyl being phenyl having from 1 to 3 substituents independently selected from the group consisting of halo, lower alkyl and lower alkyloxy;
the radical A is a member selected from the group consisting of:
(a) an isothiocyanato group —N=C=S (a);
(b) an amino radical of the formula

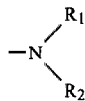

(b) wherein $R_1$ and $R_2$ are each independently selected from the group consisting of hydrogen and lower alkyl;
(c) a radical of the formula

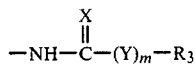

(c), wherein X is selected from the group consisting of O and S, Y is selected from the group consisting of O and NH, m is the integer 0 or 1, and $R_3$ is selected from the group consisting of hydrogen, lower alkyl, mono- and dihalo-(lower alkyl), phenyl and substituted phenyl, said substituted phenyl having from 1 to 2 substituents independently selected from the group consisting of halo, lower alkyl and lower alkyloxy, provided that:
(i) when said X is S, then said Y is NH and said m is 1, and
(ii) when said Y is O and said m is 1, then said $R_3$ is other than hydrogen; and
(d) a radical of the formula

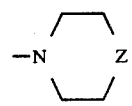

(d) wherein Z is a member selected from the group consisting of a direct bond, $CH_2$, O and $N-R_4$, wherein $R_4$ is selected from the group consisting of hydrogen, lower alkyl, hydroxy-(lower alkyl), (lower alkyloxy)-lower alkyl, lower alkanoyl, lower alkylsulfonyl, phenylmethylsulfonyl, lower alkyloxycarbonyl, lower alkyloxycarbonylmethyl, phenoxycarbonyl, aminocarbonyl, mono- and di(-lower alkyl)aminocarbonyl, aminocarbonylmethyl, (lower alkyl) aminocarbonylmethyl, (lower alkyl)aminothioxomethyl, (lower alkylthio)thioxomethyl, phenyl, phenylmethyl, benzoyl and substituted benzoyl, said substituted benzoyl being benzoyl having from 1 to 2 substituents independently selected from the group consisting of halo, lower alkyl and lower alkyloxy; and R is a member selected from the group consisting of hydrogen and nitro, provided that when said R is nitro, then said A is amino.

As used throughout the specification, the term "lower alkyl" denotes straight and branch chained hydrocarbon radicals having from 1 to 6 carbon atoms, such as, for example, methyl, ethyl, 1-methylethyl, 1,1'-dimethylethyl, propyl, butyl, pentyl, hexyl and the like; "lower alkanoyl" is meant to include straight and branch chained alkanoyl radicals having from 1 to 6 carbon atoms such as, for example, formyl, acetyl, propanoyl, 2-methylpropanoyl, butanoyl, pentanoyl, hexanoyl and the like; and the term "halo" is generic to halogens of atomic weight less than 127, i.e., fluoro, chloro, bromo and iodo.

Preferred compounds within the scope of formula (I) are those wherein Q stands for CH and R represents hydrogen. Particularly preferred compounds are those wherein Ar is mono- or dihalophenyl, most preferably 2,4-dichlorophenyl.

In order to simplify the structural representation of compounds (I) and of certain starting materials and intermediates used in the preparation thereof, the 2-Ar-2-(1H-imidazol-1-ylmethyl or 1H-1,2,4-triazol-1-ylmethyl)-1,3-dioxolan-4-yl group, wherein Ar has the previously indicated meaning, will hereinafter be represented by the symbol D:

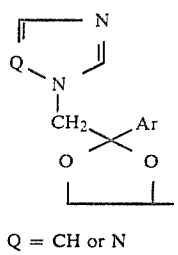

Q = CH or N

Compounds of formula (I) wherein A is a radical of the formula (b), a radical of the formula (c) wherein R₃ is other than hydrogen when m is 1, or a radical of formula (d) wherein R₄ is other than hydroxy-lower alkyl, said A being represented by $A_1$ and said compounds by (I-a), can be prepared by the reaction of an appropriate reactive ester of formula (II) with an appropriately substituted phenol of formula (III).

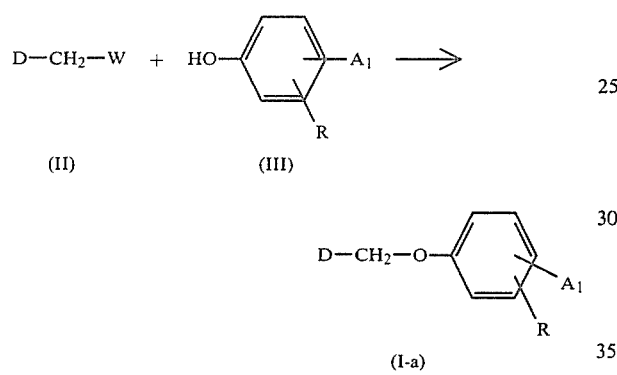

In formula (II), W is a reactive ester residue such as, for example, halo, methylsulfonyloxy, 4-methylphenylsulfonyloxy and the like.

The reaction of (II) with (III) may be carried out following standard O-alkylating procedures, e.g., by stirring the reactants together at somewhat elevated temperatures and in the presence of and appropriate base, in a suitable reaction-inert organic solvent such as, for example, 4-methyl-2-pentanone, N,N-dimethylformamide, N,N-dimethylacetamide, dimethylsulfoxide and the like, or mixtures of such solvents with, for example, aromatic hydrocarbons, e.g. benzene, methylbenzene and the like. Appropriate bases which may advantageously be employed include alkali and earth alkali metal carbonates, hydrogen carbonates, hydrides and the like, e.g. sodium carbonate, sodium hydrogen carbonate, potassium carbonate, sodium hydride and the like.

When $A_1$ in (I-a) is an amino radical of formula (b) wherein at least one of $R_1$ and $R_2$ is hydrogen, (I-a-1), or an unsubstituted 1-piperazinyl-radical, (I-a-2), it is appropriate to use in the foregoing preparation a phenol (III) wherein said amino, respectively piperazinyl, group is protected with an appropriate protecting group P, (III-a) and (III-b) respectively, in order to avoid N-alkylation, and, to eliminate the protecting group of the thus obtained (I-a-3) and (I-a-4) by classical means. Appropriate protecting groups include, for example, lower alkanoyl and lower alkyloxycarbonyl groups which may easily be removed by alkaline hydrolysis.

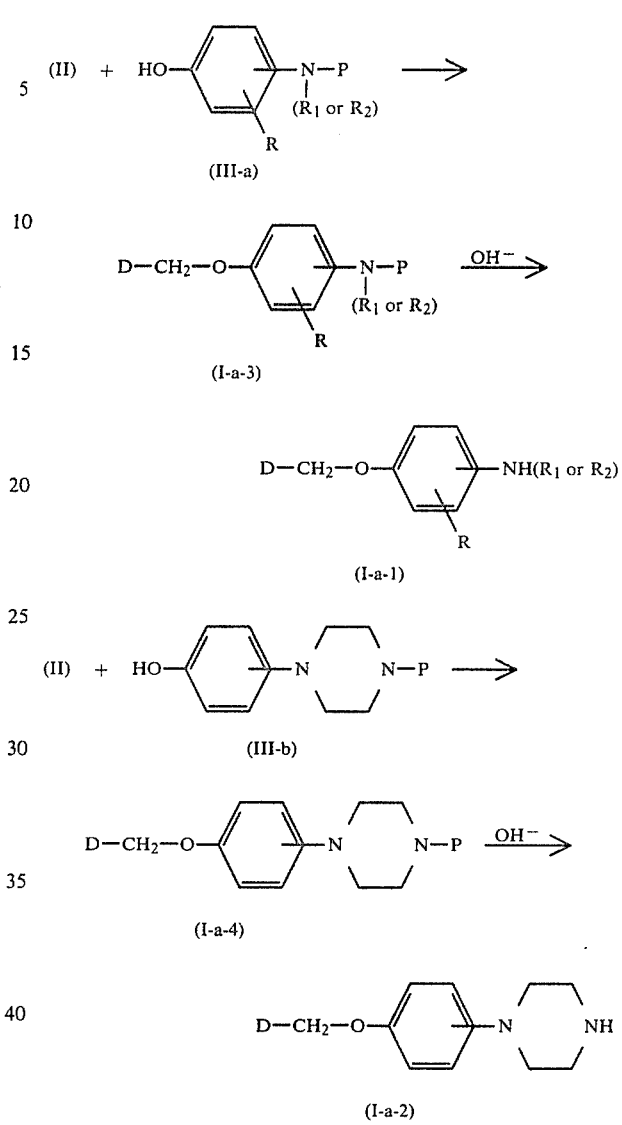

Compounds of formula (I) wherein A stands for an isothiocyanato group, i.e., wherein A has the formula (a), said compounds being represented by (I-b), can easily be derived from a compound (I-a-1) wherein ($R_1$ or $R_2$) and R are all hydrogen, (I-a-1'), following art-known methodologies of preparing isothiocyanates starting from amines, e.g., by the reaction of (I-a-1') with carbon disulfide in the presence of N,N'-methanetetraylbis [cyclohexanamine] in pyridine.

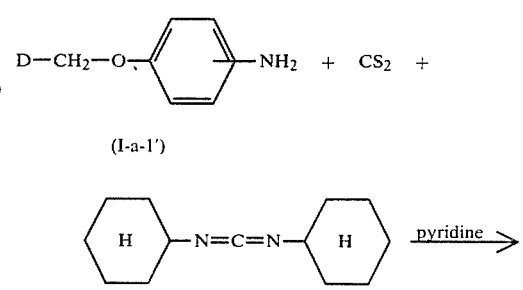

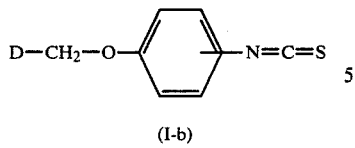

(I-b)

Compounds of formula (I) wherein A is an aminothiocarbonylamino radical; i.e., a radical of formula (c) wherein X is S, Y is NH, m is 1 and $R_3$ is hydrogen, said compounds being represented by (I-c) can be prepared by reacting the corresponding (I-b) with ammonium hydroxide in a suitable solvent such as, for example, a lower alkanol, e.g. methanol, ethanol and the like.

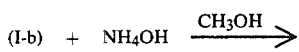

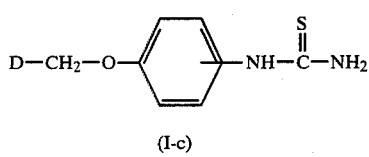

(I-c)

Compounds of formula (I) wherein A has the formula (c) wherein Y is NH and m is 1, and, wherein X is O when $R_3$ is hydrogen, (I-d), are conveniently obtained by the reaction of an appropriate amine (I-a-1') with an appropriate isocyanate or isothiocyanate of formula (IV).

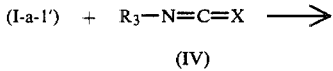

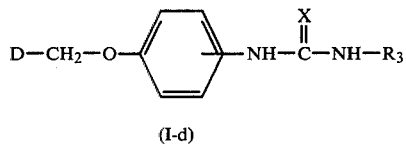

(I-d)

The foregoing reaction may be carried out according to art-known methodologies, e.g., by stirring the reactants together, preferably while heating, in an appropriate reaction-inert solvent, e.g., 1,4-dioxane. When $R_3$ stands for hydrogen, in which case (IV) represents hydrocyanic acid, it is appropriate to use an appropriate alkali metal cyanate in aqueous medium, the free acid being liberated by the addition thereto of an appropriate acid, e.g., acetic acid.

Compounds of formula (I) wherein A has the formula (c) wherein X and Y are each O and $R_3$ and m are as previously defined, (I-e), can be prepared by acylating an appropriate amine (I-a-1') with an appropriate acylating agent according to common N-acylating procedures. Suitable acylating agents which may be used to prepare compounds (I-e) wherein m is zero include acyl halides and anhydrides derived from the acid $R_3COOH$ and also the acid itself, the latter being preferred when formylation is desired. In order to prepare compounds (I-e) wherein m is 1 there may be used appropriate carbonohalidates, preferably carbonochloridates, and di($R_3$)carbonates.

(I-a-1') $\xrightarrow{\text{acylation}}$

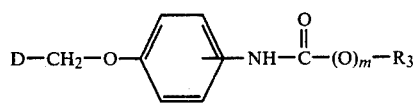

(I-e)

Compounds of formula (I) wherein A has the formula (d) wherein Z stands for N-$R_4$ and said $R_4$ for an aminocarbonyl, a lower alkylaminocarbonyl or a (lower alkyl)aminothiocarbonyl radical, said compounds being represented by the formula (I-f) wherein $R_5$ is hydrogen or lower alkyl, may be prepared starting from an appropriate piperazine of formula (I-a-2) by the addition thereto of an appropriate isocyanate or isothiocyanate of formula (V) wherein X is O or S, provided that when said $R_5$ is hydrogen, then said X is O, following similar procedures as described herein for the preparation of compounds (I-d) starting from (I-a-1') and (IV).

(I-a-2) + $R_5$—N=C=X $\longrightarrow$ (V)

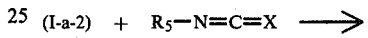

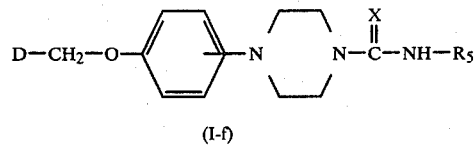

(I-f)

Compounds of formula (I) wherein A has the formula (d) wherein Z is N-$R_4$ and said $R_4$ is selected from the group consisting of lower alkyl, hydroxy(lower alkyl), lower alkyloxycarbonylmethyl, aminocarbonylmethyl, (lower alkyl)aminocarbonylmethyl and phenylmethyl said $R_4$ being represented by $R_4'$ and said compounds by the formula (I-g), can be derived from a compound (I-a-2) by alkylating the latter with an appropriate reactive ester of formula (VI) wherein W and $R_4'$ are as previously defined, following standard N-alkylating procedures as generally known in the art.

(I-a-2) + W—$R'_4$ $\longrightarrow$ (VI)

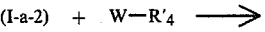

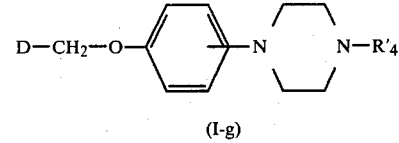

(I-g)

When $R_4'$ in formula (I-g) stands for a hydroxyethyl radical the same compounds may also be obtained by the reaction of (I-a-2) with oxirane e.g. by bubbling the latter through a heated solution of (I-a-2) in a suitable organic solvent such as a lower alkanol, e.g. methanol, ethanol or 2-propanol.

When $R_4'$ in formula (I-g) represents a primary or secondary lower alkyl group or a phenylmethyl group said compounds may also be prepared from (I-a-2) and an appropriate aldehyde or ketone according to a reductive amination reaction, for example, by hydrogenating a mixture of the reactants in an appropriate reaction-inert organic solvent such as a lower alkanol, e.g., methanol or ethanol, in the presence of an appropriate catalyst such as, for example, palladium-on-charcoal, and an appropriate base such as sodium acetate.

Compounds of formula (I-g) wherein $R_4'$ represents a (lower alkyl)aminocarbonylmethyl radical may also be derived from the corresponding compounds (I-g) wherein $R_4'$ is lower alkyloxycarbonylmethyl by the reaction of the latter with an appropriate lower alkanamine following art-known procedures of preparing amides starting from esters.

Compounds of formula (I) wherein A has the formula (d) wherein Z is $NR_4$ and said $R_4$ is an acyl radical selected from the group consisting of lower alkanoyl, lower alkylsulfonyl, phenylmethylsulfonyl, lower alkyloxycarbonyl, phenoxycarbonyl, aminocarbonyl, mono- and di(lower alkyl)aminocarbonyl, benzoyl and substituted benzoyl, said $R_4$ being represented by $R_4''$ and said compounds by the formula (I-h), can conveniently be obtained by acylating an appropriate compound (I-a-2) with an appropriate acylating agent following standard N-acylating procedures. In general said acylation may be performed by the reaction of (I-a-2) with an appropriate acyl halide, derived from the corresponding carboxylic or sulfonic acid, or, when the acyl group to be introduced is lower alkanoyl, benzoyl or substituted benzoyl by the reaction with an anhydride of the corresponding acid or with the acid itself, the latter being preferred when formylation is desired. When the acyl group to be introduced is lower alkyloxycarbonyl or phenoxycarbonyl there may also be used an appropriate di(lower alkyl)or diphenyl carbonate as an acylating agent.

(I-a-2) $\xrightarrow{\text{acylation}}$

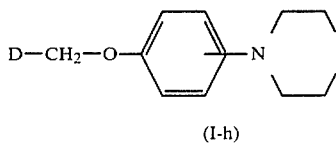

(I-h)

Compounds of formula (I-h) wherein $R_4''$ stands for lower alkanoyl may if desired be reduced with an appropriate reducing agent such as, for example, lithium aluminium hydride to obtain a corresponding compound of formula (I-g) wherein $R_4'$ is a lower alkyl group which is unbranched at the α-carbon atom.

Compounds of formula (I) wherein A has the formula (d) wherein Z stands for $N-R_4$ and said $R_4$ is a (lower alkylthio)thioxomethyl group, (I-i), can be derived from (I-a-2) by reacting the latter with carbon disulfide and an appropriate alkylating agent to introduce the lower alkyl group, e.g. a di(lower alkyl) sulfate, in an appropriate solvent such as, for example, a mixture of a lower alkanol, e.g., methanol, and water.

(I-a-2) + $CS_2$ + alkylating agent $\longrightarrow$

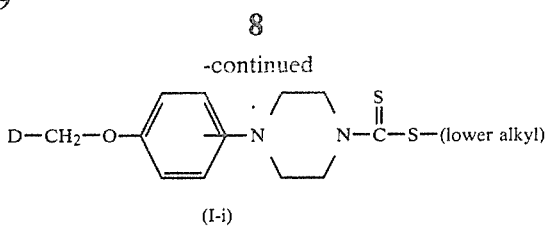

(I-i)

Compounds of formula (I) wherein A has the formula (d) wherein Z stands for $N-R_4$ and said $R_4$ is (lower alkyloxy)lower alkyl are easily derived from the corresponding hydroxy(lower alkyl)-substituted compounds by alkylating the latter according to art-known O-alkylating procedures as previously described herein for the preparation of the compounds (I-a) starting from (II) and (III).

Compounds of the formulae (I-a-1') and (I-b) as well as compounds of formula (I-e) wherein $R_3$ is phenyl and m is 1, and compounds of formula (I-e) wherein m is zero and $R_3$ is lower alkyl are also described in our application Ser. No. 764,265, filed Jan. 31, 1977, and subsequently filed as a continuation-in-part application on even date with this application.

Starting materials of formula (II) wherein Q stands for CH and methods of preparing the same are described in Belg. Pat. No. 837,831. In general the reactive esters of formula (II) can be prepared along the following sequence of reactions.

An appropriate 1-Ar-2-bromoethanone of formula (VII) is subjected to a ketalization reaction with 1,2,3-propanetriol following methodologies analogous to those described in Synthesis, 1974 (I), 23.

In a preferred manner of carrying out the reaction both reactants are refluxed together for several hours with azeotropic water removal in an appropriate organic solvent, preferably in the presence of a simple alcohol, such as, for example, ethanol, propanol, butanol, pentanol and the like, and in the presence of an appropriate strong acid such as 4-methylbenzenesulfonic acid. Suitable organic solvents are, for example, aromatic hydrocarbons, such as benzene, methylbenzene, dimethylbenzene and the like and saturated hydrocarbons, such as cyclohexane.

The thus obtained dioxolane (VIII) is then reacted with benzoyl chloride to obtain a benzoate of the formula (IX) and the latter is subsequently reacted with 1H-imidazole or 1H-1,2,4-triazole. Said reaction is preferably carried out by stirring and heating the reactants together in a suitable organic solvent, e.g. N,N-dimethylformamide, in the presence of an appropriate strong metal base, e.g. sodium methanolate to obtain an intermediate of the formula (X). The desired reactive esters of formula (II) are then conveniently prepared by first hydrolyzing (X) in alkaline medium and thereafter converting the hydroxy group of the thus obtained (XI) into a reactive ester thereof according to methodologies generally known in the art. For example, methanesulfonates and 4-methylbenzenesulfonates are conveniently prepared by the reaction of the alcohol with methanesulfonyl chloride or 4-methylbenzenesulfonyl chloride and halides may be prepared by the reaction of the alcohol with an appropriate halogenating agent such as, for example, sulfuryl chloride, phosphor pentachloride, phosphor pentabromide, phosphoryl chloride and the like. When the reactive ester is an iodide, it is preferably prepared from the corresponding chloride or bromide by the replacement of that halogen with iodine.

The foregoing reactions may be illustrated as follows:

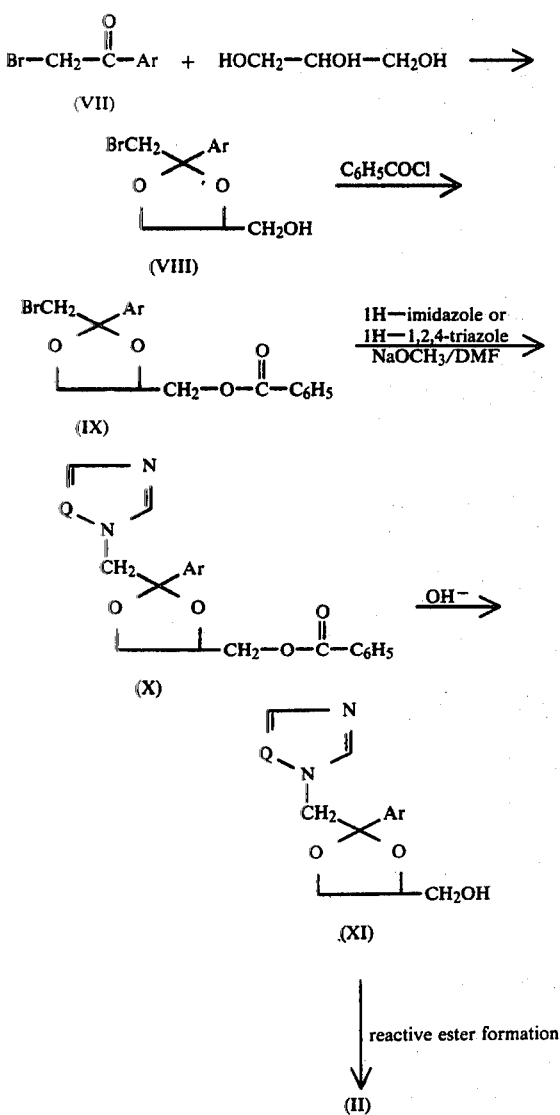

An important number of the starting materials of formula (III) are also known compounds and the remaining may generally be derived from aminophenols and (1-piperazinyl)phenols following art-known procedures as previously described herein for the preparation of the required A-groups in compounds (I) starting from (I-a-1) and (I-a-2). When the phenolic hydroxyl group would interfere with such synthetic procedures it is appropriate to first protect said group with an appropriate protecting group, the latter being removed at a later stage. For example, the protected phenol may take the form of a methoxy-compound, the methoxy group of which is ultimately transformed into the desired hydroxy group by the treatment of the former with an appropriate strong acid, e.g., hydrobromic acid, or there may be used an acyloxy compound, the acyl group of which can be removed by alkaline hydrolysis.

The compounds of formula (I) have basic properties and thus may be converted to their therapeutically useful acid addition salts by reaction with an appropriate acid, as, for example, an inorganic acid such as hydrohalic acid, i.e., hydrochloric, hydrobromic or hydroiodic acid; sulfuric, nitric or thiocyanic acid; a phosphoric acid; and organic acid such as acetic, propanoic, hydroxyacetic, 2-hydroxypropanoic, 2-oxopropanoic, ethanedioic, propanedioic, 1,4-butanedioic, (Z)-2-butenedioic, (E)-2-butenedioic, 2-hydroxy-1,4-butanedioic, 2,3-dihydroxy-1,4-butanedioic, 2-hydroxy-1,2,3-propanetricarboxylic, benzoic, 3-phenyl-2-propenoic, α-hydroxybenzeneacetic, methanesulfonic, ethanesulfonic, 2-hydroxyethanesulfonic, 4-methylbenzenesulfonic, 2-hydroxybenzoic, 4-amino-2-hydroxybenzoic, 2-phenoxybenzoic or 2-acetyloxybenzoic acid. The salts are in turn converted to the corresponding free bases in the usual manner, e.g. by reaction with alkali such as sodium or potassium hydroxide.

From formula (I) it is evident that the compounds of this invention have at least two asymmetric carbon atoms in their structures, namely those located in the 2- and 4-positions of the dioxolane nucleus, and consequently they can exist under different stereochemically isomeric forms. The stereochemically isomeric forms of (I) and the pharmaceutically acceptable acid addition salts thereof are intended to be within the scope of this invention.

The diastereomeric racemates of (I), denoted as cis and trans forms respectively, according to the rules described in C.A., 76, Index Guide, Section IV, p. 85 (1972), may be obtained separately by conventional methods. Appropriate methods which may advantageously be employed therefore include, for example, selective crystallization and chromatography separation, e.g. column chromatography.

Since the stereochemical configuration is already fixed in the intermediates (II) it is also possible to separate cis and trans forms at this or even an earlier stage, whereupon the corresponding forms of (I) may be derived therefrom in the previously indicated manner. The separation of cis and trans forms of such intermediates may be performed by conventional methods as described hereabove for the separation of cis and trans forms of the compounds (I).

It is evident that the cis and trans diastereomeric racemates may be further resolved into their optical isomers, cis(+), cis(−), trans(+) and trans(−) by the application of methodologies known to those skilled in the art.

The compounds of formula (I) and the pharmaceutically acceptable acid addition salts thereof are useful agents in combatting fungi and bacteria. For example, said compounds and acid addition salts thereof were found to be highly active against a wide variety of fungi such as, for example, *Microsporum canis, Ctenomyces mentagrophytes, Trichophyton rubrum, Phialophora verrucosa, Cryptococcus neoformans, Candida tropicalis, Candida albicans, Mucor* species, *Aspergillus fumigatus, Sporotrichum schenckii* and *Saprolegnia* species, and against bacteria such as, for example, *Erysipelotrix insidiosa,* Staphylococci such as *Staphylococcus hemolyticus* and Streptococci such as *Streptococcus pyogenes.* In view of the potent, local as well as systemic, antimicrobial activity the compounds of this invention constitute useful tools for the destruction or prevention of the growth of fungi and bacteria and more particularly they can effectively be used in the treatment of subjects suffering from such microorganism.

The strong antimicrobial activity of the compounds (I) is clearly evidenced by the data obtained in the following experiments, which data is only given to illustrate the useful antimicrobial properties of all the compounds (I) and not to limit the invention either with respect to the scope of susceptible microorganisms nor with respect to the scope of formula (I).

Experiment A: Activity of compounds (I) against vaginal candidosis in rats.

Female Wistar rats of ±100 g body weight were used. They were ovariectomized and hysterectomized and after three weeks of recovery, 100 μg of oestradiol undecylate in sesame oil was given subcutaneously once a week for 3 consecutive weeks. The thus induced pseudo-oestrus was controlled by microscopic examination of vaginal smears. Food and water were left available ad libitum.

The rats were infected intravaginally with $8.10^5$ cells of Candida albicans, grown on Sabouraud broth for 48 hours at 37° C. and diluted with saline. The date of infection varied from day +25 to day +32 after surgical intervention, depending on the appearance of signs of induced pseudo-oestrus.

The drugs under investigation were administered orally once a day for two days starting from the day of infection. For each experiment there were placebo treated controls. The results were assessed by taking vaginal smears with sterile swabs on several days after infection. The swabs were put into Sabouraud broth in petri-dishes and incubated for 48 hours at 37° C. If no growth of Candida albicans occured, i.e., when the animals were negative at the end of the experiment, this was due to drug administration because it never happened in placebo treated controls.

The Tables I, II and III below give the lowest oral dose of the drug under investigation which was found active at the 14th day after infection.

Experiment B: Activity of compounds (I) against crop candidosis in turkeys.

Turkeys of 14 days old were infected in the crop with $4.10^6$ Candida albicans cells, grown on Sabouraud broth for 48 hours at 37° C. and diluted with saline. The volume of the inoculum was 1 ml. The drug under investigation were premixed in 500 mg of lacton and thereafter admixed in 1000 g of meal without any additives. The concentration of the drug under investigation in the meal was expressed in mg/kg.

The animals were given the medicated feed for 13 consecutive days starting on the day of infection. At the end of the experiment all animals were sacrificed. At autopsy the crops were removed, emptied and grinded in an ultra-turrax mixer in 15 ml of sterile saline. Colony counting was done on Sabouraud agar and the results given in the Tables I, II and III represent the $ED_{50}$, i.e., the dose of the drug whereby the crops of 50% of the animals were completely negative for Candida albicans.

TABLE I

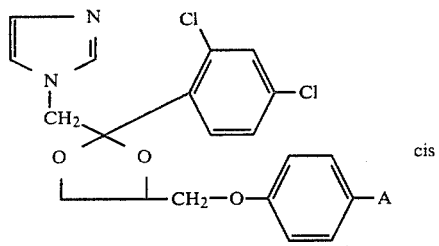

| A | Base or Salt | Vaginal candidosis in rats: lowest effective oral dose in mg/kg | Crop candidosis in turkeys: $ED_{50}$ in mg/kg of feed. |
|---|---|---|---|
| —N=C=S | base | 5 | 125 |
| —NH$_2$ | base | 5 | 125 |
| —N(CH$_3$)$_2$ | 2(COOH)$_2$H$_2$O | 10 | 31 |
| —NH—CHO | base | 2.5 | 31 |
| —NH—CO—CH$_3$ | base | 5 | 31 |
| —NH—CO—C$_2$H$_5$ | (COOH)$_2$ (CH$_3$)$_2$—CHOH | 10 | 31 |
| —NH—CO—CH(Cl)$_2$ | base | 10 | 125 |
| —NH—CO—C$_6$H$_5$ | base | 5 | 63 |
| —NH—CO—C$_6$H$_4$—F | base | 5 | 16 |
| —NH—CO—C$_6$H$_4$—Cl | base | — | 31 |
| —NH—CO—C$_6$H$_4$—Br | base | 10 | 31 |

TABLE I-continued

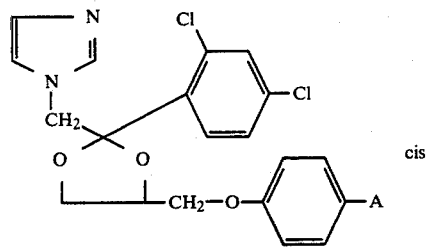
cis

| A | Base or Salt form | Vaginal candidosis in rats: lowest effective oral dose in mg/kg. | Crop candidosis in turkeys: Ed$_{50}$ in mg/kg of feed. |
|---|---|---|---|
| —NH—CO—⟨⟩—OCH$_3$ | base | 40 | 16 |
| —NH—CO—OCH$_3$ | HNO$_3$ | 5 | 31 |
| —NH—CO—OC$_2$H$_5$ | base | 5 | 16 |
| —NH—CO—O—⟨⟩ | base | 10 | |
| —NH—CO—NH—CH$_3$ | base | 10 | 125 |
| —NH—CO—NH—C$_2$H$_5$ | base | 10 | 125 |
| —NH—CS—NH$_2$ | base | 20 | — |
| —NH—CS—NH—CH$_3$ | base | 10 | 125 |
| —NH—CS—NH—C$_2$H$_5$ | base | 5 | 125 |
| —N⟨pyrrolidine⟩ | base | — | 16 |
| —N⟨morpholine⟩ | base | 2.5 | 16 |
| —N⟨piperazine⟩NH | base | 5 | 125 |
| —N⟨piperazine⟩N—CHO | base | <10 | — |
| —N⟨piperazine⟩N—CO—CH$_3$ | base | 2.5 | 8 |
| —N⟨piperazine⟩N—CO—OCH$_3$ | base | 2.5 | 8 |
| —N⟨piperazine⟩N—CO—OC$_2$H$_5$ | base | 2.5 | 16 |
| —N⟨piperazine⟩N—CO—NH$_2$ | base | 5 | 125 |
| —N⟨piperazine⟩N—CO—NH—CH$_3$ | base.H$_2$O | 2.5 | 16 |
| —N⟨piperazine⟩N—CO—NH—C$_2$H$_5$ | base.H$_2$O | 10 | 125 |

TABLE I-continued

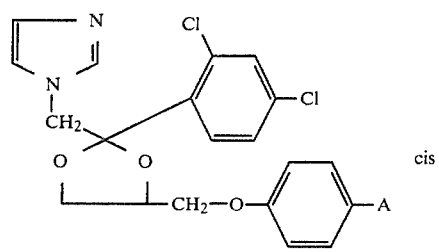

cis

| A | Base or Salt form | Vaginal candidosis in rats: lowest effective oral dose in mg/kg. | Crop candidosis in turkeys: Ed$_{50}$ in mg/kg of feed. |
|---|---|---|---|
| −N⟨⟩N−CO−NH−(CH$_2$)$_2$−CH$_3$ | base.2H$_2$O | 2.5 | 125 |
| −N⟨⟩N−CS−NH−CH$_3$ | base.H$_2$O | 2.5 | 125 |
| −N⟨⟩N−CH$_2$−CH$_3$ | 2(COOH)$_2$ | 1.25 | 31 |
| −N⟨⟩N−COO−CH$_3$ | 2HCl | 2.5 | 8 |
| −N⟨⟩N−COO−C$_2$H$_5$ | 2HCl.½ H$_2$O | 10 | 31 |
| −N⟨⟩N−CH$_3$ | 2(COOH)$_2$. C$_2$H$_5$OH | 2.5 | — |
| −N⟨⟩N−CH$_2$−CH(CH$_3$)$_2$ | 3HCl.H$_2$O | — | 16 |
| −N⟨⟩N−CH(CH$_3$)$_2$ | 3HCl. CH$_3$−CHOHCH$_3$ | 2.5 | — |
| −N⟨⟩N−(CH$_2$)$_3$−CH$_3$ | 3HCl.H$_2$O | — | 31 |
| −N⟨⟩N−(CH$_2$)$_2$−CH$_3$ | base.2½ (COOH)$_2$ | 2.5 | 16 |
| −NH−CH$_2$−CH$_3$ | base | 2.5 | 31 |
| −NH−CH$_3$ | base | 5 | — |
| −N⟨⟩N−SO$_2$−CH$_3$ | base.H$_2$O | 1.25 | 31 |
| −N⟨⟩N−CH$_2$−C$_6$H$_5$ | 3HCl.H$_2$O | 2.5 | 31 |

TABLE I-continued

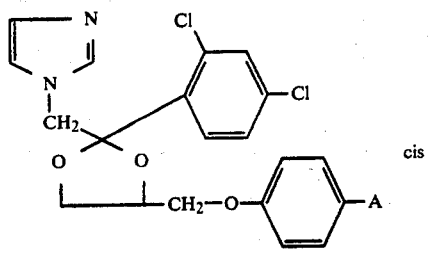

| A | Base or Salt form | Vaginal candidosis in rats: lowest effective oral dose in mg/kg. | Crop candidosis in turkeys: Ed$_{50}$ in mg/kg of feed. |
|---|---|---|---|
| $-N\diagdown N-SO_2-CH_2-C_6H_5$ | base | — | 16 |
| $-N\diagdown N-CH_2-CO-NH_2$ | base | 1.25 | — |
| $-N\diagdown N-CH_2-CH_3$ | base | <2.5 | — |
| $-N\diagdown N-CH_2-C_6H_5$ | base | 1.25 | 16 |

TABLE II

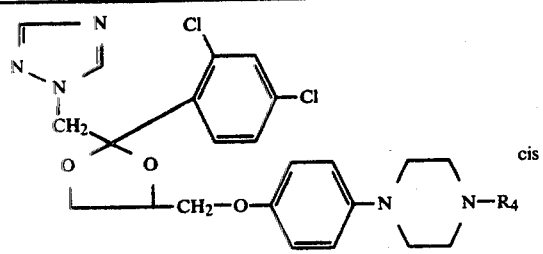

TABLE II-continued

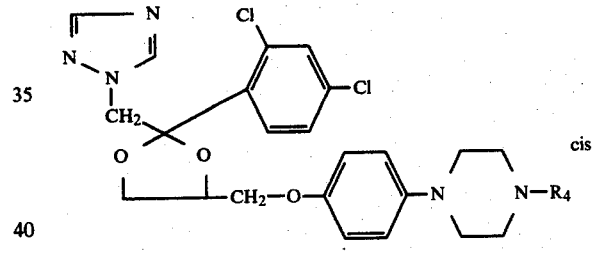

| R$_4$ | Base or Salt form | Vaginal candidosis in rats: lowest effective oral dose in mg/kg. | Crop candidosis in turkeys: ED$_{50}$ in mg/kg of feed. | R$_4$ | Base or Salt form | Vaginal candidosis in rats: lowest effective oral dose in mg/kg. | Crop candidosis in turkeys: ED$_{50}$ in mg/kg of feed. |
|---|---|---|---|---|---|---|---|
| (CH$_2$)$_3$—CH$_3$ | base | — | 16 | CO—O—CH$_3$ | base | — | 8 |
| CH(CH$_3$)—CH$_2$—CH$_3$ | base | 2.5 | 63 | SO$_2$—CH$_2$—C$_6$H$_5$ | base.H$_2$O | — | 16 |
| CO—C$_2$H$_5$ | 2HCl | — | 8 | CO—O—C$_6$H$_5$ | base | — | 16 |
| CO—O—C$_2$H$_5$ | 2HCl | — | 8 | (CH$_2$)$_2$—CH$_3$ | base | — | 16 |
| CHO | base | 1.25 | 16 | CO—CH$_3$ | base | 1.25 | 8 |
| CO—(CH$_2$)$_2$—CH$_3$ | 2HCl | — | 16 | CH$_3$ | base | 1.25 | 16 |
| CH$_2$—CH(CH$_3$)$_2$ | base | 2.5 | 31 | SO$_2$—CH$_3$ | base.1.2H$_2$O | 1.25 | 31 |
| CH(CH$_3$)$_2$ | base | 2.5 | — | CO—C$_6$H$_5$ | base | 1.25 | — |

TABLE III

Compounds of formula (I).

| Q | Ar | A | R | Isomer | Base or Salt form | Vaginal candidosis in rats: lowest effective oral dose in mg/kg. | Crop candidosis in turkeys: ED$_{50}$ in mg/kg of feed. |
|---|---|---|---|---|---|---|---|
| CH | 4-OCH$_3$—C$_6$H$_4$ | 4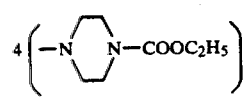 | H | — | ½ (E)— HOOC—CH=CH— COOH | 2.5 | — |

TABLE III-continued

Compounds of formula (I).

| Q | Ar | A | R | Isomer | Base or Salt form | Vaginal candidosis in rats: lowest effective oral dose in mg/kg. | Crop candidosis in turkeys: $ED_{50}$ in mg/kg of feed. |
|---|---|---|---|---|---|---|---|
| CH | 4-OCH$_3$—C$_6$H$_4$ | 4(—N⟨⟩N—CO—CH$_3$) | H | — | base | — | 31 |
| CH | 2,4-Cl$_2$—C$_6$H$_3$ | 3(—NH—CO—CH$_3$) | H | cis | HNO$_3$ | 10 | 63 |
| CH | 2,4-Cl$_2$—C$_6$H$_3$ | 3(—N⟨⟩N—COOC$_2$H$_5$) | H | cis | base | 2.5 | — |
| CH | 2,4-Cl$_2$—C$_6$H$_3$ | 4-NH$_2$ | 3-NO$_2$ | cis | base | 5.0 | 31 |

In view of their antifungal and antibacterial properties this invention provides valuable compositions comprising the subject compounds of formula (I) or acid addition salts thereof as the active ingredient in a solvent or a solid, semi-solid or liquid diluent or carrier, and, in addition, it provides an effective method of combatting fungal or bacterial growth by use of an effective antifungal or antibacterial amount of such compounds (I) or salts thereof. Antifungal and antibacterial compositions comprising an effective amount of an active compound (I), either alone or in combination with other active therapeutic ingredients, in admixture with suitable carriers may be readily prepared according to conventional pharmaceutical techniques for the usual routes of administration. Preferred compositions are in dosage unit form, comprising per dosage unit an effective quantity of the active ingredient in admixture with suitable carriers. Although the amount of the active ingredient per unit dosage may vary within rather wide limits, dosage units comprising from about 50 to about 500 mg and more particularly from about 100 to about 250 mg of the active ingredient are preferred.

The following examples are intended to illustrate and not to limit the scope of the present invention. Unless otherwise stated all parts therein are by weight.

EXAMPLE I

A mixture of 2.4 parts of N-(4-hydroxyphenyl)-benzamide, 4.2 parts of cis-2-(2,4-dichlorophenyl)-2-(1H-imidazol-1-ylmethyl)-1,3-dioxolan-4-ylmethyl methanesulfonate, 2 parts of potassium carbonate and 75 parts of dimethylsulfoxide is stirred overnight at 100° C. The reaction mixture is cooled and poured onto water. The product is extracted twice with trichloromethane. The combined extracts are washed twice with water, dried, filtered and evaporated. The residue is crystallized from 1-butanol. The product is filtered off and dried, yielding 2.7 parts (51%) of cis-N-{4-[2-(2,4-dichlorophenyl)-2-(1H-imidazol-1-ylmethyl)-1,3-dioxolan-4-ylmethoxy]phenyl}benzamide; mp. 217.6° C.

EXAMPLE II

Following the procedure of Example I and using therein an equivalent amount of an appropriate substituted N-(4-hydroxyphenyl)benzamide as a starting material the following compounds are prepared:

cis-N-{4-[2-(2,4-dichlorophenyl)-2-(1H-imidazol-1-ylmethyl)-1,3-dioxolan-4-ylmethoxy]phenyl}-4-methoxybenzamide; mp. 188.7° C.;

cis-N-{4-[2-(2,4-dichlorophenyl)-2-(1H-imidazol-1-ylmethyl)-1,3-dioxolan-4-ylmethoxy]phenyl}-4-fluorobenzamide; mp. 198.2° C.;

cis-ethyl {4-[2-(2,4-dichlorophenyl)-2-(1H-imidazol-1-ylmethyl)-1,3-dioxolan-4-ylmethoxy]phenyl} carbamate; mp. 178.9° C.; and cis-4-bromo-N-{4-[2-(2,4-dichlorophenyl)-2-(1H-imidazol-1-ylmethyl)-1,3-dioxolan-4-ylmethoxy]phenyl]benzamide; mp. 217.9° C.

EXAMPLE III

A mixture of 2.8 parts of 4-chloro-N-(4-hydroxyphenyl)benzamide, 0.4 parts of sodium hydride dispersion 78%, 75 parts of dimethylsulfoxide and 18 parts of benzene is stirred for one hour at 40° C. Then there are added 4.2 parts of cis-2-(2,4-dichlorophenyl)-2-(1H-imidazol-1-ylmethyl)-1,3-dioxolan-4-ylmethyl methanesulfonate and the whole is stirred overnight at 100° C. The reaction mixture is cooled and poured onto water. The product is extracted twice with benzene. The combined extracts are washed with water, dried, filtered and evaporated. The residue is crystallized from 1-butanol. The product is filtered off and dried, yielding 3.2 parts (58%) of cis-4-chloro-N-{4-[2-(2,4-dichlorophenyl)-2-(1H-imidazol-1-ylmethyl)1,3-dioxolan-4-ylmethoxy]phenyl}benzamide; mp. 213.3° C.

EXAMPLE IV

A mixture of 1.8 parts of 4-(1-pyrrolidinyl)-phenol, 0.4 parts of sodium hydride dispersion 78% and 100 parts of dimethylsulfoxide is stirred for one hour at 40° C. Then there are added 4.2 parts of cis-2-(2,4-dichlorophenyl)-2-(1H-imidazol-1-ylmethyl)-1,3-dioxolan-4-ylmethyl methanesulfonate and stirring is continued overnight at 100° C. The reaction mixture is cooled and poured onto water. The product is extracted with 1,1'-oxybisethane. The extract is washed twice with water, dried, filtered and evaporated. The residue is crystallized from 1,1'-oxybisbutane. The product is filtered off and dried, yielding 2.3 parts (48%) of cis-1-{2-(2,4-dichlorophenyl)-4-[4-(1-pyrrolidinyl)phenoxymethyl]-1,3-dioxolan-2-ylmethyl}-1H-imidazole; mp. 149.1° C.

EXAMPLE V

A mixture of 1.9 parts of 4-(4-morpholinyl)-phenol, 4.2 parts of cis-2-(2,4-dichlorophenyl)-2-(1H-imidazol-1-ylmethyl)-1,3-dioxolan-4-ylmethyl methanesulfonate, 2 parts of potassium carbonate and 80 parts of 4-methyl-2-pentanone is stirred and refluxed overnight. The reaction mixture is cooled, water is added and the product is extracted twice with 1,1'-oxybisethane. The combined extracts are dried, filtered and evaporated. The residue is purified by column-chromatography over silica gel using trichloromethane as eluent. The pure fractions are collected and the eluent is evaporated. The residue is crystallized from 1,1'-oxybisbutane, yielding, After drying, 2.3 parts (47%) of cis-4{4-[2-(2,4-dichlorophenyl)-2-(1H-imidazol-1-ylmethyl)-1,3-dioxolan-4-ylmethoxy]-phenyl}morpholine; mp. 135° C.

EXAMPLE VI

A mixture of 1.9 parts of 4-(dimethylamino)-phenol hydrochloride, 4.2 parts of cis-2-(2,4-dichlorophenyl)-2-(1H-imidazol-1-ylmethyl)-1,3-dioxolan-4-ylmethyl methanesulfonate, 4 parts of potassium carbonate and 80 parts of 4-methyl-2-pentanone is stirred and refluxed overnight. The reaction mixture is cooled, water is added and the product is extracted twice with 1,1'-oxybisethane. The combined extracts are washed with water, dried, filtered and evaporated. The residue is converted into the ethanedioate salt in 2-propanone and 2,2'-oxybispropane. The salt is filtered off and crystallized from ethanol, yielding 2.4 parts (37%) of cis-4-[2-(2,4-dichlorophenyl)-2-(1H-imidazol-1-ylmethyl)-1,3-dioxolan-4-ylmethoxy]-N,N'-dimethylbenzenamine diethanedioate.hydrate; mp. 112.5° C.

EXAMPLE VII

A mixture of 1.8 parts of N-(4-hydroxyphenyl)-propanamide, 4.2 parts of cis-2-(2,4-dichlorophenyl)-2-(1H-imidazol-1-ylmethyl)-1,3-dioxolan-4-ylmethyl methanesulfonate, 2 parts of potassium carbonate and 67.5 parts of N,N-dimethylformamide is stirred and heated overnight at 100° C. The reaction mixture is cooled and poured onto water. The product is extracted twice with benzene. The combined extracts are washed with water, dried, filtered and evaporated. The residue is converted into the ethanedioate salt in 4-methyl-2-pentanone and 2,2'-oxybispropane. The salt is filtered off and crystallized from 2-propanol. The product is filtered off and dried over week-end at 80° C., yielding 2.3 parts (37%) of cis-N-{4-[2-(2,4-dichlorophenyl)-2-(1H-imidazol-1-ylmethyl)-1,3-dioxolan-4-ylmethoxy]phenyl}propanamide ethanedioate. 2-propanolate; mp. 116.9° C.

EXAMPLE VIII

A mixture of 1.7 parts of N-(4-hydroxyphenyl)-acetamide, 4.2 parts of cis-2-(2,4-dichlorophenyl)-2-(1H-imidazol-1-ylmethyl)-1,3-dioxolan-4-ylmethyl methanesulfonate, 2 parts of potassium carbonate and 68 parts of N,N-dimethylformamide is stirred overnight at 100° C. The reaction mixture is cooled and poured onto water. The product is extracted twice with trichloromethane. The combined extracts are washed twice with water, dried, filtered and evaporated. The residue is triturated in a mixture of 4-methyl-2-pentanone and 2,2'-oxybispropane. The product is filtered off and crystallized from 4-methyl-2-pentanone, yielding 2.8 parts (61%) of cis-N-{4-[2-(2,4-dichlorophenyl)-2-(1H-imidazol-1-ylmethyl)-1,3-dioxolan-4-ylmethoxy]phenyl}acetamide; mp. 180.5° C.

A mixture of 8.9 parts of cis-N-{4-[2-(2,4-dichlorophenyl)-2-(1H-imidazol-1-ylmethyl)-1,3-dioxolan-4-ylmethoxy]phenyl}acetamide, 1.5 parts of potassium hydroxide and 80 parts of 1-butanol is stirred and refluxed overnight. The reaction mixture is evaporated and water is added to the residue. The precipitated product is filtered off and crystallized from methylbenzene, yielding 6.6 parts (82%) of cis-4-[2-(2,4-dichlorophenyl)-2-(1H-imidazol-1-ylmethyl)-1,3-dioxolan-4-ylmethoxy]benzenamine; mp. 164.4° C.

EXAMPLE IX

A mixture of 0.8 parts of isothiocyanatomethane, 4.2 parts of cis-4-[2-(2,4-dichlorophenyl)-2-(1H-imidazol-1-ylmethyl)-1,3-dioxolan-4-ylmethoxy]benzenamine, and 100 parts of 1,4-dioxane is stirred and refluxed for 3 hours. The solvent is evaporated and the residue is crystallized from 4-methyl-2-pentanone. The product is filtered off and recrystallized from acetonitrile, yielding 2.7 parts (53%) of cis-N-{4-[2-(2,4-dichlorophenyl)-2-(1H-imidazol-1-ylmethyl)-1,3-dioxolan-4-ylmethoxy]phenyl}-N'-methylthiourea; mp. 130.7° C.

EXAMPLE X

Following the procedure of Example IX and using an equivalent amount of isothiocyanatoethane in place of the isothiocyanatomethane used therein, there is prepared:

cis-N-{4-[2-(2,4-dichlorophenyl)-2-(1H-imidazol-1-ylmethyl)-1,3-dioxolan-4-ylmethoxy]phenyl}-N'-ethylthiourea; mp. 140.4° C.

EXAMPLE XI

To a stirred solution of 4.2 parts of cis-4-[2-(2,4-dichlorophenyl)-2-(1H-imidazol-1-ylmethyl)-1,3-dioxolan-4-ylmethoxy]benzenamine in 10 parts of acetic acid are added 20 parts of water. Then there is added a solution of 1 part of potassium isocyanate in 20 parts of water and the whole is stirred for one hour at room temperature. After the addition of 200 parts of water, the mixture is neutralized with potassium carbonate. The product is extracted with trichloromethane. The extract is dried, filtered and evaporated. The residue is crystallized from 4-methyl-2-pentanone. The product is filtered off and recrystallized from 4-methyl-2-pentanone, yielding 2.9 parts (62%) of cis-N-{4-[2-(2,4-dichlorophenyl)-2-(1H-imidazol-1-ylmethyl)-1,3-dioxolan-4-ylmethoxy]phenyl}-urea; mp. 155.1° C.

EXAMPLE XII

A mixture of 1 part of isocyanatomethane, 4.2 parts of cis-4-[2-(2,4-dichlorophenyl)-2-(1H-imidazol-1-ylmethyl)-1,3-dioxolan-4-ylmethoxy]benzenamine and 75 parts of 1,4-dioxane is stirred overnight at room temperature. The reaction mixture is evaporated and the residue is crystallized from 4-methyl-2-pentanone. The product is filtered off and dried, yielding 3.5 parts (73%) of cis-N-{4-[2-(2,4-dichlorophenyl)-2-(1H-imidazol-1-ylmethyl)-1,3-dioxolan-4-ylmethoxy]phenyl}-N'-methylurea; mp. 169° C.

EXAMPLE XIII

Following the procedure of Example XII and using an equivalent amount of respectively isocyanatoethane and isocyanatobenzene in place of the isocyanatomethane used therein, there are prepared respectively:

cis-N-{4-[2-(2,4-dichlorophenyl)-2-(1H-imidazol-1-ylmethyl)-1,3-dioxolan-4-ylmethoxy]phenyl}-N'-ethylurea; mp. 154.3° C.; and cis-N-{4-[2-(2,4-dichlorophenyl)-2-(1H-imidazol-1-ylmethyl)-1,3-dioxolan-4-ylmethoxy]phenyl}-N'-phenylurea nitrate; mp. 127.3° C.

EXAMPLE XIV

A mixture of 40 parts of formic acid and 4.2 parts of cis-4-[2-(2,4-dichlorophenyl)-2-(1H-imidazol-1-ylmethyl)-1,3-dioxolan-4-ylmethoxy]benzamine is stirred and refluxed for 48 hours. The reaction mixture is cooled and evaporated. The residue is dissolved in water and neutralized with sodium hydrogen carbonate. The product is extracted twice with trichloromethane. The combined extracts are dried, filtered and evaporated. The residue is crystallized from a mixture of 4-methyl-2-pentanone and 2,2'-oxybispropane, yielding 3.8 parts (85%) of cis-N-{4-[2-(2,4-dichlorophenyl)-2-(1H-imidazol-1-ylmethyl)-1,3-dioxolan-4-ylmethoxy]phenyl}formamide; mp. 132.6° C.

EXAMPLE XV

A mixture of 1.8 parts of methyl carbonochloridate, 4.2 parts of cis-4-[2-(2,4-dichlorophenyl)-2-(1H-imidazol-1-ylmethyl)-1,3-dioxolan-4-ylmethoxy]benzenamine, 2 parts of potassium carbonate and 75 parts of 1,4-dioxane is stirred and refluxed for one hour. The reaction mixture is cooled and poured onto water. Upon the addition of 2,2'-oxybispropane, the product is precipitated. It is filtered off and converted into the nitrate salt in 2-propanone and 2,2'-oxybispropane. The salt is filtered off and crystallized from acetonitrile, yielding 3.4 parts (63%) of cis-methyl {4-[2-(2,4-dichlorophenyl)-2-(1H-imidazol-1-ylmethyl-1,3-dioxolan-4-ylmethoxy]phenyl}-carbamate nitrate; mp. 157.6° C.

EXAMPLE XVI

A mixture of 1.7 parts of dichloroacetyl chloride, 4.2 parts of cis-4-[2-(2,4-dichlorophenyl)-2-(1H-imidazol-1-ylmethyl)-1,3-dioxolan-4-ylmethoxy]benzenamine, 2 parts of potassium carbonate and 100 parts of 1,4-dioxane is stirred and refluxed for 4 hours. The reaction mixture is cooled and poured onto water. The product is extracted twice with 1,1'-oxybisethane. The combined extracts are dried, filtered and evaporated. The residue is crystallized from 4-methyl-2-pentanone. The product is filtered off and dried, yielding 3.9 parts (73%) of cis-2,2-dichloro-N-{4-[2-(2,4-dichlorophenyl)-2-(1H-imidazol-1-ylmethyl)-1,3-dioxolan-4-ylmethoxy]phenyl}acetamide; mp. 165.6° C.

EXAMPLE XVII

To a stirred and cooled (ice-bath) solution of 8.4 parts of cis-4-[2-(2,4-dichlorophenyl)-2-(1H-imidazol-1-ylmethyl)-1,3-dioxolan-4-ylmethoxy]benzenamine in 75 parts of pyridine and 112 parts of trichloromethane are added dropwise 3.5 parts of phenyl carbonochloridate. Upon completion, stirring is continued for 3 hours at room temperature. The reaction mixture is poured onto water and the product is extracted twice with trichloromethane. The combined extracts are dried, filtered and evaporated. The residue is triturated in a mixture of 1,1'-oxybisethane and 2,2'-oxybispropane. The product is filtered off and crystallized from 4-methyl-2-pentanone, yielding 8.6 parts of cis phenyl {4-[2-(2,4-dichlorophenyl)-2-(1H-imidazol-1-ylmethyl)-1,3-dioxolan-4-ylmethoxy]phenyl}carbamate; mp. 170.6° C.

EXAMPLE XVIII

To a stirred and cooled (ice-salt bath) solution of 13 parts of carbon disulfide and 2.1 parts of N,N'-methanetetraylbis[cyclohexanamine] in 15 parts of pyridine is added dropwise a solution of 4.2 parts of cis-4-[2-(2,4-dichlorophenyl)-2-(1H-imidazol-1-ylmethyl)-1,3-dioxolan-4-ylmethoxy]benzenamine in 25 parts of pyridine at a temperature between −10° C. and −5° C. Upon completion, stirring is continued first at −10°-−5° C. for 3 hours and further at room temperature for one hour. The reaction mixture is evaporated. The residue is dissolved in 20 parts of acetic acid. The solution is stirred and 50 parts of water are added. The formed precipitate is filtered off and the filtrate is neutralized with potassium carbonate. The product is extracted with 1,1'-oxybisethane. The extract is dried, filtered and evaporated. The residue is purified by column-chromatography over silica gel using trichloromethane as eluent. The pure fractions are collected and the eluent is evaporated. The residue is crystallized from a mixture of 4-methyl-2-pentanone and 2,2'-oxybispropane. The product is filtered off and dried, yielding 3.2 parts (69%) of cis-1-[2-(2,4-dichlorophenyl)-4-(4-isothiocyanatophenoxymethyl)-1,3-dioxolan-2-ylmethyl]-1H-imidazole; mp. 136° C.

EXAMPLE XIX

A mixture of 90 parts of ammonium hydroxide, 5 parts of cis-1-[2-(2,4-dichlorophenyl)-4-(4-isothiocyanatophenoxymethyl)-1,3-dioxolan-2-ylmethyl]-1H-imidazole and 200 parts of methanol is stirred for 3 hours at room temperature. The reaction mixture is poured onto water and the product is extracted with trichloromethane. The extract is washed with water, dried, filtered and evaporated. The residue is purified by column-chromatography over silica gel using a mixture of trichloromethane and methanol (98:2 by volume) as eluent. The pure fractions are collected and the eluent is evaporated. The residue is crystallized from 4-methyl-2-pentanone, yielding 2.8 parts (54%) of cis-N-{4-[2-(2,4-dichlorophenyl)-2-(1H-imidazol-1-ylmethyl)-1,3-dioxolan-4-ylmethoxy]phenyl}thiourea; mp. 190.4° C.

EXAMPLE XX

A. A mixture of 33.8 parts of 4-(1-piperazinyl)-phenol dihydrobromide, 11.2 parts of acetic acid anhydride, 42 parts of potassium carbonate and 300 parts of 1,4-dioxane is stirred and refluxed for 3 days. The reaction mixture is filtered and the filtrate is evaporated. The solid residue is stirred in water and sodium hydrogen carbonate is added. The whole is stirred for 30 minutes. The precipitated product is filtered off and dissolved in a diluted hydrochloric acid solution. The solution is extracted with trichloromethane. The acid aqueous phase is separated and neutralized with ammonium hydroxide. The product is filtered off and crystallized from ethanol, yielding 5.7 parts of 1-acetyl-4-(4-hydroxyphenyl)-piperazine; mp. 181.3° C.

B. A mixture of 2.4 parts of 1-acetyl-4-(4-hydroxyphenyl)piperazine, 0.4 parts of sodium hydride dispersion 78%, 75 parts of dimethylsulfoxide and 22.5 parts of benzene is stirred for one hour at 40° C. Then there are added 4.2 parts of cis-2-(2,4-dichlorophenyl)-2-(1H-imidazol-1-ylmethyl)-1,3-dioxolan-4-ylmethyl methanesulfonate and stirring is continued overnight at 100° C. The reaction mixture is cooled and diluted with water.

The product is extracted with 1,1'-oxybisethane. The extract is dried, filtered and evaporated. The residue is crystallized from 4-methyl-2-pentanone. The product is filtered off and dried, yielding 3.2 parts (59%) of cis-1-acetyl-4-{4-[2-(2,4-dichlorophenyl)-2-(1H-imidazol-1-ylmethyl)-1,3-dioxolan-4-ylmethoxy]phenyl}piperazine; mp. 146° C.

EXAMPLE XXI

A mixture of 21 parts of cis-1-acetyl-4-{4-[2-(2,4-dichlorophenyl)-2-(1H-imidazol-1-ylmethyl)-1,3-dioxolan-4-ylmethoxy]phenyl}piperazine, 10 parts of potassium hydroxide and 200 parts of 1-butanol is stirred and refluxed overnight. The reaction mixture is cooled and benzene is added. The whole is washed with water, dried, filtered and evaporated. The residue is crystallized from 4-methyl-2-pentanone. The product is filtered off and dried, yielding 13.9 parts (71%) of cis-1-{4-[2-(2,4-dichlorophenyl)-2-(1H-imidazol-1-ylmethyl)-1,3-dioxolan-4-ylmethoxy]phenyl }-piperazine; mp. 170.7° C.

EXAMPLE XXII

A mixture of 0.9 parts of isothiocyanatomethane, 4.9 parts of cis-1{4-[2-(2,4-dichlorophenyl)-2-(1H-imidazol-1-ylmethyl)-1,3-dioxolan-4-ylmethoxy]phenyl}piperazine and 100 parts of 1,4-dioxane is stirred overnight at room temperature. The precipitated product is filtered off and crystallized from 1,4-dioxane. It is filtered off again and recrystallized from 4-methyl-2-pentanone, yielding 2.7 parts (47%) of cis-4-{4-[2-(2,4-dichlorophenyl)-2-(1H-imidazol-1-ylmethyl)-1,3-dioxolan-4-ylmethoxy]phenyl}-N-methyl-1-piperazinecarbothioamide monohydrate; mp. 138.2° C.

EXAMPLE XXIII

A mixture of 1 part of isothiocyanatoethane, 4.9 parts of cis-1-{4-[2-(2,4-dichlorophenyl)-2-(1H-imidazol-1-ylmethyl)-1,3-dioxolan-4-ylmethoxy]phenyl}-piperazine and 130 parts of dichloromethane is stirred for 3 hours at room temperature. The reaction mixture is evaporated and the residue is triturated in a mixture of 4-methyl-2-pentanone and 2,2'-oxybispropane. The product is filtered off and crystallized from 4-methyl-2-pentanone, yielding 5.2 parts (89%) of cis-4-{4-[2-(2,4-dichlorophenyl)-2-(1H-imidazol-1-ylmethyl)-1,3-dioxolan-4-ylmethoxy]phenyl}-N-ethyl-1-piperazinecarbothioamide.hemihydrate; mp. 187.9° C.

EXAMPLE XXIV

A mixture of 0.7 parts of isocyanatomethane, 4.9 parts of cis-1-{4-[2-(2,4-dichlorophenyl)-2-(1H-imidazol-1-ylmethyl)-1,3-dioxolan-4-ylmethoxy]phenyl}-piperazine and 100 parts of 1,4-dioxane is stirred overnight at room temperature. The solvent is evaporated. The residue is purified by column-chromatography over silica gel using a mixture of trichloromethane and methanol (98:2 by volume) as eluent. The pure fractions are collected and the eluent is evaporated. The residue is crystallized from 4-methyl-2-pentanone. The product is filtered off and dried, yielding 3.7 parts (66%) of cis-4-{4-[2-(2,4-dichlorophenyl)-2-(1H-imidazol-1-ylmethyl)-1,3-dioxolan-4-ylmethoxy]phenyl}-N-methyl-1-piperazinecarboxamide monohydrate; mp. 120.6° C.

EXAMPLE XXV

Following the procedure of Example XXIV and using equivalent amounts of respectively isocyanatoethane and isocyanatopropane in place of the isocyanatomethane used therein, the following compounds are respectively obtained:

cis-4-{4-[2-(2,4-dichlorophenyl)-2-(1H-imidazol-1-ylmethyl)-1,3-dioxolan-4-ylmethoxy]phenyl}-N-ethyl-1-piperazinecarboxamide monohydrate; mp. 121.2° C; and cis-4-{4-[2-(2,4-dichlorophenyl)-2-(1H-imidazol-1-ylmethyl)-1,3-dioxolan-4-ylmethoxy]phenyl}-N-propyl-1-piperazinecarboxamide dihydrate; mp. 111.1° C.

EXAMPLE XXVI

A mixture of 1 part of potassium isocyanate, 4.9 parts of cis-1-{4-[2-(2,4-dichlorophenyl)-2-(1H-imidazol-1-ylmethyl)-1,3-dioxolan-4-ylmethoxy]phenyl}-piperazine, 0.6 parts of acetic acid, 50 parts of water and 50 parts of 1,4-dioxane is stirred overnight at room temperature. The solvent is evaporated and the residue is purified by column-chromatography over silica gel using a mixture of trichloromethane and methanol (98:2 by volume) as eluent. The pure fractions are collected and the eluent is evaporated. The residue is crystallized from 4-methyl-2-pentanone. The product is filtered off and dried, yielding 2 parts (38%) of cis-4-{4-[2-(2,4-dichlorophenyl)-2-(1H-imidazol-1-ylmethyl)-1,3-dioxolan-4-ylmethoxy]phenyl}-1-piperazinecarboxamide; mp. 189.8° C.

EXAMPLE XXVII

A mixture of 1.2 parts of methyl carbonochloridate, 4.9 parts of cis-1-{4-[2-(2,4-dichlorophenyl)-2-(1H-imidazol-1-ylmethyl)-1,3-dioxolan-4-ylmethoxy]-phenyl}-piperazine, 2 parts of sodium hydrogen carbonate, 100 parts of 1,4-dioxane and 50 parts of water is stirred overnight at room temperature. Water is added to the reaction mixture. The precipitated product is filtered off and crystallized from 4-methyl-2-pentanone, yielding 3.8 parts (69%) of cis-methyl 4-{4-[2-(2,4-dichlorophenyl)-2-(1H-imidazol-1-ylmethyl)-1,3-dioxolan-4-ylmethoxy]phenyl}-1-piperazinecarboxylate; mp. 137.5° C.

EXAMPLE XXVIII

Following the procedure of Example XXVII there is prepared cis-ethyl 4-{4-[2-(2,4-dichlorophenyl)-2-(1H-imidazol-1-ylmethyl)-1,3-dioxolan-4-ylmethoxy]-phenyl}-1-piperazinecarboxylate; mp. 112.2° C. by the reaction of ethyl carbonochloridate with cis-1-{4-[2-(2,4-dichlorophenyl)-2-(1H-imidazol-1-ylmethyl)-1,3-dioxolan-4-ylmethoxy]-phenyl}piperazine.

EXAMPLE XXIX

A mixture of 60 parts of formic acid and 4.9 parts of cis-1-{4-[2-(2,4-dichlorophenyl)-2-(1H-imidazol-1-ylmethyl)-1,3-dioxolan-4-ylmethoxy]phenyl}piperazine is stirred and refluxed overnight. The reaction mixture is cooled, water is added and the whole is alkalized with a sodium hydroxide solution 50%. The product is extracted with trichloromethane. The extract is dried, filtered and evaporated. The residue is crystallized from 4-methyl-2-pentanone, yielding 5.3 parts (100%) of cis-4-{4-[2-(2,4-dichlorophenyl)-2-(1H-imidazol-1-ylmethyl)-1,3-dioxolan-4-ylmethoxy]phenyl}-1-piperazinecarboxaldehyde; mp. 153.4° C.

EXAMPLE XXX

A mixture of 2 parts of dimethylcarbamic chloride, 4.9 parts of cis-1-{4-[2-(2,4-dichlorophenyl)-2-(1H-imidazol-1-ylmethyl)-1,3-dioxolan-4-ylmethoxy]-phenyl}-piperazine, 4 parts of potassium carbonate, 130 parts of dichloromethane and 20 parts of water is stirred for 3 hours at room temperature. The reaction mixture is diluted with water and the whole is stirred overnight at room temperature. The dichloromethane-phase is separated and the solvent is evaporated. The residue is triturated in a mixture of 4-methyl-2-pentanone and 2,2'-oxybispropane. The product is filtered off and recrystallized from 4-methyl-2-pentanone, yielding 4.8 parts (86%) of cis-4-{4-[2-(2,4-dichlorophenyl)-2-(1H-imidazol-1-ylmethyl)-1,3-dioxolan-4-ylmethoxy]-phenyl}-N,N-dimethyl-1-piperazinecarboxamide; mp. 143.8° C.

EXAMPLE XXXI

A mixture of 1.5 parts of benzoyl chloride, 4.9 parts of cis-1-{4-[2-(2,4-dichlorophenyl)-2-(1H-imidazol-1-ylmethyl)-1,3-dioxolan-4-ylmethoxy]phenyl}piperazine, 3 parts of potassium carbonate, 130 parts of dichloromethane and 20 parts of water is stirred for one hour at room temperature. Water is added and the whole is stirred for 2 hours at room temperature. The organic phase is separated, dried, filtered and evaporated. The residue is converted into the ethanedioate salt in 2-propanone. The salt is filtered off and crystallized from a mixture of ethanol and 2,2'-oxybispropane, yielding 5.9 parts (80%) of cis-1-benzoyl-4-{4-[2-(2,4-dichlorophenyl)-2-(1H-imidazol-1-ylmethyl)-1,3-dioxolan-4-ylmethoxy]phenyl}-piperazine ethanedioate (2:3) hemihydrate; mp. 132.9° C.

EXAMPLE XXXII

A mixture of 1.5 parts of propanoic acid anhydride, 4.9 parts of cis-1-{4-[2-(2,4-dichlorophenyl)-2-(1H-imidazol-1-ylmethyl)-1,3-dioxolan-4-ylmethoxy]-phenyl}-piperazine, 2 parts of potassium carbonate and 130 parts of dichloromethane is stirred first for 2 hours and further after the addition of 20 parts of water, for one hour at room temperature. The layers are separated and the organic phase is evaporated. The residue is crystallized from 4-methyl-2-pentanone. The product is filtered off, treated with potassium carbonate and recrystallized from 4-methyl-2-pentanone, yielding 3.6 parts (66%) of cis-1-{4-[2-(2,4-dichlorophenyl)-2-(1H-imidazol-1-ylmethyl)-1,3-dioxolan-4-ylmethoxy]-phenyl}-4-(1-oxopropyl)piperazine; mp. 122.7° C.

EXAMPLE XXXIII

A mixture of 10 parts of carbon disulfide, 19.6 parts of cis-1-{4-[2-(2,4-dichlorophenyl)-2-(1H-imidazol-1-ylmethyl)-1,3-dioxolan-4-ylmethoxy]phenyl}piperazine, 2.4 parts of sodium hydroxide, 80 parts of methanol and 100 parts of water is stirred for 3 hours at room temperature. Then there are added 7.5 parts of dimethyl sulfate and stirring is continued for one hour at room temperature. Water is added and the product is extracted with dichloromethane. The extract is dried, filtered and evaporated. The residue is triturated in 4-methyl-2-pentanone. The product is filtered off and crystallized from ethanol, yielding 23.1 parts (100%) of cis-methyl 4-{4-[2-(2,4-dichlorophenyl)-2-(1H-imidazol-1-ylmethyl)-1,3-dioxolan-4-ylmethoxy]-phenyl}-1-piperazinecarbodithioate; mp. 132.9° C.

EXAMPLE XXXIV

A mixture of 1.7 parts of phenyl carbonochloridate, 4.9 parts of cis-1-{4-[2-(2,4-dichlorophenyl)-2-(1H-imidazol-1-ylmethyl)-1,3-dioxolan-4-ylmethoxy]-phenyl}-piperazine, 2 parts of potassium carbonate and 130 parts of dichloromethane is stirred first for 2 hours at room temperature and further, after the addition of 20 parts of water, for one hour at the same temperature. From the reaction mixture the organic phase is separated and evaporated. The residue is triturated in a mixture of 4-methyl-2-pentanone and 2,2'-oxybispropane. The product is filtered off and crystallized from 4-methyl-2-pentanone, yielding 5.3 parts (87%) of cis-phenyl 4-{4-[2-(2,4-dichlorophenyl)-2-(1H-imidazol-1-ylmethyl)-1,3-dioxolan-4-ylmethoxy]phenyl}-1-piperazinecarboxylate; mp. 159.5° C.

EXAMPLE XXXV

Following the procedure of Example XX-B and using equivalent amounts of the appropriate starting materials the following compounds are still obtained:

trans-1-acetyl-4-{4-[2-(2,4-dichlorophenyl)-2-(1H-imidazol-1-yl-methyl)-1,3-dioxolan-4-ylmethoxy]-phenyl}piperazine;

1-acetyl-4-{4-[2-(4-chlorophenyl)-2-(1H-imidazol-1-ylmethyl)-1,3-dioxolan-4-ylmethoxy]phenyl}piperazine;

1-acetyl-4-{4-[2-(4-bromophenyl)-2-(1H-imidazol-1-ylmethyl)-1,3-dioxolan-4-ylmethoxy]phenyl}piperazine;

1-acetyl-4-{4-[2-(4-fluorophenyl)-2-(1H-imidazol-1-ylmethyl)-1,3-dioxolan-4-ylmethoxy]phenyl}piperazine;

1-acetyl-4-{4-[2-(2,6-dichlorophenyl)-2-1H-imidazol-1-ylmethyl)-1,3-dioxolan-4-ylmethoxy]phenyl}piperazine;

1-acetyl-4-{4-[2-(1H-imidazol-1-ylmethyl)-2-(4-methylphenyl)-1,3-dioxolan-4-ylmethoxy]phenyl}-piperazine; and 1-acetyl-4-{4-[2-(1H-imidazol-1-ylmethyl)-2-(4-chloro-2-methylphenyl)-1,3-dioxolan-4-ylmethoxy]phenyl}piperazine.

EXAMPLE XXXVI

A mixture of 174 parts of 2-bromo-1-(3-chlorophenyl)-ethanone, 81 parts of 1,2,3-propanetriol, 7.4 parts of 4-methylbenzenesulfonic acid, 94 parts of 1-butanol and 528 parts of benzene is stirred and refluxed for 20 hours with water-separator. The reaction mixture is poured onto a diluted sodium hydroxide solution and the layers are separated. The aqueous phase is extracted twice with methylbenzene. The combined organic phases are washed twice with water, dried, filtered and evaporated, yielding 238 parts of cis+trans-2-(bromomethyl)-2-(3-chlorophenyl)-1,3-dioxolane-4-methanol as a residue.

238 Parts of cis+trans-2-(bromomethyl)-2-(3-chlorophenyl)-1,3-dioxolane-4-methanol are dissolved in a mixture of 144 parts of pyridine and 1135 parts of trichloromethane and the solution is cooled to about 5° C. Then there are added dropwise 149 parts of benzoyl chloride at a temperature below 10° C. Upon completion, stirring is continued for 2 hours at room temperature. The reaction mixture is poured onto water and the layers are separated. The aqueous phase is extracted twice with trichloromethane. The combined extracts are washed twice with water, dried, filtered and evaporated. The residue is stirred for a few hours in hexane.

The precipitated product is filtered off and dried at the air, yielding 128 parts of cis+trans-[2-(bromomethyl)-2-(3-chlorophenyl)-1,3-dioxolan-4-ylmethyl] benzoate.

A mixture of 26 parts of 1H-imidazole and 68.5 parts of sodium methanolate solution 30% is stirred and refluxed for 15 minutes. 90 Parts of N,N-dimethylformamide are added and the methanol is distilled off till an internal temperature of 130° C. Then there is added dropwise a solution of 102.5 parts of cis+trans-[2-(bromomethyl)-2-(3-chlorophenyl)-1,3-dioxolan-4-ylmethyl] benzoate in 225 parts of N,N-dimethylformamide. Upon completion, stirring is continued for 3 hours at reflux. The reaction mixture is cooled, water is added and the product is extracted three times with 4-methyl-2-pentanone. The combined extracts are washed twice with water, dried, filtered and evaporated, yielding 43 parts of cis+trans-[2-(3-chlorophenyl)-2-(1H-imidazol-1-ylmethyl)-1,3-dioxolan-4-ylmethyl] benzoate as a residue.

A mixture of 45 parts of cis+trans-[2-(3-chlorophenyl)-2-(1H-imidazol-1-ylmethyl)-1,3-dioxolan-4-ylmethyl] benzoate, 36 parts of sodium hydroxide solution 50%, 600 parts of 1,4-dioxane and 200 parts of water is stirred and refluxed for 1 hour. The reaction mixture is cooled and poured onto water. Trichloromethane is added and the layers are separated. The organic phase is washed with water, dried, filtered and evaporated. The residue is converted into the hydrochloride salt in 2-propanone and 2-propanol. After stirring for 2 hours in an ice-bath, the salt is filtered off and dried, yielding 14 parts of cis+trans-2-(3-chlorophenyl)-2-(1H-imidazol-1-ylmethyl)-1,3-dioxolane-4-methanol monohydrochloride; mp. 198.3° C.

A mixture of 68 parts of cis+trans-2-(3-chlorophenyl)-2-(1H-imidazol-1-ylmethyl)-1,3-dioxolane-4-methanol and 570 parts of pyridine is cooled to 0° C. The ice-bath is taken away and 26.3 parts of methanesulfonyl chloride are added dropwise (exothermic reaction: temp. rises to 20° C.). Upon completion, stirring is continued for 3 hours at room temperature. The reaction mixture is poured onto water and the product is extracted with trichloromethane. The extract is dried, filtered and evaporated. The residue is converted into the hydrochloride salt in 2-propanone and 2-propanol. The salt is filtered off and crystallized from 2-propanol, yielding 32 parts of [2-(3-chlorophenyl)-2-(1H-imidazol-1-ylmethyl)-1,3-dioxolan-4-ylmethyl] methanesulfonate monohydrochloride.

EXAMPLE XXXVII

Following the procedure of Example XXXVI and using equivalent amounts of the appropriate starting materials, the following methanesulfonates are prepared:

[2-(1H-imidazol-1-ylmethyl)-2-(3-methylphenyl)-1,3-dioxolan-4-ylmethyl] methanesulfonate; and
[2-(1H-imidazol-1-ylmethyl)-2-(4-methoxyphenyl)-1,3-dioxolan-4-ylmethyl] methanesulfonate.

EXAMPLE XXXVIII

A mixture of 1.6 parts of 1H-1,2,4-triazole, 54 parts of N,N-dimethylformamide and 45 parts of benzene is stirred and refluxed for 2 hours. After cooling, 0.78 parts of sodium hydride dispersion 78% are added and the whole is stirred for 30 minutes at room temperature. Then there are added 8.9 parts of cis-2-(bromomethyl)-2-(2,4-dichlorophenyl)-1,3-dioxolan-4-ylmethyl benzoate and stirring is continued overnight at 150° C. The reaction mixture is cooled and poured onto water. The product is extracted three times with benzene. The combined extracts are washed twice with water, dried, filtered and evaporated, yielding 8.5 parts of cis-[2-(2,4-dichlorophenyl)-2-(1H-1,2,4-triazol-1-ylmethyl)-1,3-dioxolan-4-ylmethyl] benzoate as a residue.

A mixture of 289 parts of cis-[2-(2,4-dichlorophenyl)-2-(1H-1,2,4-triazol-1-ylmethyl)-1,3-dioxolan-4-ylmethyl] benzoate, 200 parts of sodium hydroxide solution 50%, 1500 parts of 1,4-dioxane and 300 parts of water is stirred and refluxed for 2 hours. The reaction mixture is cooled and poured onto water. The product is extracted with dichloromethane. The extract is washed with water, dried, filtered and evaporated. The residue is purified by column-chromatography over silica gel using a mixture of trichloromethane and methanol (95:5 by volume) as eluent. The first fraction is collected and the eluent is evaporated, yielding 89 parts of cis-2-(2,4-dichlorophenyl)-2-(1H-1,2,4-triazol-1-ylmethyl)-1,3-dioxolane-4-methanol; mp. 138.2° C.

A mixture of 30.6 parts of cis-2-(2,4-dichlorophenyl)-2-(1H-1,2,4-triazol-1-ylmethyl)-1,3-dioxolane-4-methanol and 75 parts of pyridine is stirred at room temperature and there are added dropwise 17.2 parts of methanesulfonyl chloride. Upon completion, stirring is continued overnight at room temperature. The reaction mixture is poured onto ice-water and the product is extracted twice with dichloromethane. The combined extracts are washed twice with a diluted hydrochloric acid solution and twice with water, dried, filtered and evaporated. The residue is purified by column-chromatography over silica gel using a mixture of trichloromethane and methanol (95:5 by volume) as eluent. The first fraction is collected and the eluent is evaporated, yielding 21 parts of cis-[2-(2,4-dichlorophenyl)-2-(1H-1,2,4-triazol-1-ylmethyl)-1,3-dioxolan-4-methyl] methanesulfonate; mp. 98° C.

EXAMPLE XXXIX

A mixture of 13.2 parts of 1-(4-methoxyphenyl)piperazine dihydrochloride, 5.1 parts of 1-butanal, 9 parts of sodium acetate and 80 parts of methanol is hydrogenated at normal pressure and at room temperature with 1 part of palladium-on-charcoal catalyst. After the calculated amount of hydrogen is taken up, the catalyst is filtered off and the filtrate is evaporated. Water is added to the residue and the product is precipitated. It is filtered off, washed with water and converted into the hydrochloride salt in ethanol and 2-propanol. Upon the addition of 2,2'-oxybispropane, the salt is precipitated. It is filtered off and crystallized from a mixture of ethanol and 2,2'-oxybispropane, yielding 13.1 parts (81%) of 1-butyl-4-(4-methoxyphenyl)piperazine dihydrochloride; mp. 214.2° C.

EXAMPLE XL

Following the procedure of Example XXXIX and using an equivalent amount of an appropriate aldehyde or ketone in place of the 1-butanal used therein, there are prepared:

1-(4-methoxyphenyl)-4-propylpiperazine dihydrochloride; mp. 214.7° C.
1-(4-methoxyphenyl)-4-(1-methylpropyl)piperazine dihydrochloride; mp. 223.5° C.;
1-(4-methoxyphenyl)-4-(2-methylpropyl)piperazine dihydrochloride; mp. 220.3° C.;
1-(4-methoxyphenyl)-4-(1-methylethyl)piperazine dihydrochloride; mp. 230.1° C.; and 1-(4-methoxyphenyl)-4-(phenylmethyl)piperazine dihydrochloride; mp. 234° C.

EXAMPLE XLI

A mixture of 12.5 parts of 1-butyl-4-(4-methoxyphenyl)-piperazine dihydrochloride and 150 parts of hydrobromic acid solution 48% in glacial acetic acid is stirred and refluxed overnight. The reaction mixture is evaporated and the residue is triturated in 2-propanone. The product is filtered off and crystallized from water, yielding 13.1 parts (81%) of 4-(4-butyl-1-piperazinyl)-phenol monohydrobromide; mp. 281.9° C.

EXAMPLE XLII

Following the procedure of Example XLI and using an equivalent amount of an appropriate (4-methoxyphenyl)piperazine in place of the 1-butyl-4-(4-methoxyphenyl)piperazine dihydrochloride used therein there are obtained:

4-(4-propyl-1-piperazinyl)phenol sesquihydrobromide; mp. 241.8° C.;
4-[4-(1-methylpropyl)-1-piperazinyl]phenol dihydrobromide; mp. 280.4° C.;
4-[4-(2-methylpropyl)-1-piperazinyl]phenol; mp. 179.4° C.;
4-[4-(1-methylethyl)-1-piperazinyl]phenol; mp. 247.4° C.; and
4-[4-(phenylmethyl)-1-piperazinyl]phenol monohydrobromide; mp. 264.7° C.;

EXAMPLE XLIII

A mixture of 17 parts of 4-(1-piperazinyl)phenol dihydrobromide, 7 parts of ethyl carbonochloridate, 21 parts of potassium carbonate and 250 parts of 1,4-dioxane is stirred and refluxed for 48 hours. The reaction mixture is filtered, while hot and the filtrate is evaporated. The solid residue is dissolved in a diluted hydrochloric acid solution. The solution is alkalized with ammonium hydroxide. The product is filtered off and dried, yielding 3.5 parts of ethyl 4-(4-hydroxyphenyl)-1-piperazinecarboxylate; mp. 168.8° C.

EXAMPLE XLIV

Following the procedure of Example XLIII and using an equivalent amount of respectively 2- and 3-(1-piperazinyl)phenol dihydrobromide in place of the 4-(1-piperazinyl)phenol used therein, there are prepared:
ethyl 4-(2-hydroxyphenyl)-1-piperazinecarboxylate; mp. 141.8° C.; and
ethyl 4-(3-hydroxyphenyl)-1-piperazinecarboxylate; mp. 123.4° C.

EXAMPLE XLV

To a stirred solution of 80 parts of 3-(1-piperazinyl)-phenol dihydrobromide in 360 parts of water and 180 parts of trichloromethane are added portionwise 42 parts of sodium hydrogen carbonate at 10° C. Then there are added dropwise, during a 15 minutes-period, 26 parts of acetic acid anhydride while cooling at 10° C. Upon completion, stirring is continued for 3 hours at room temperature. The precipitated product is filtered off, washed with water and crystallized from 2-propanol, yielding 37 parts (70%) of 1-acetyl-4-(3-hydroxyphenyl)-piperazine; mp. 186.1° C.

EXAMPLE XLVI

To a stirred mixture of 12.9 parts of 4-(1-piperazinyl)-phenol dihydrobromide, 40 parts of ethanol and 50 parts of water are added 12.6 parts of sodium hydrogen carbonate. Then there are added dropwise 6.4 parts of methanesulfonyl chloride at 0° C. Upon completion, stirring is continued overnight. The precipitated product is filtered off and taken up in water. The whole is alkalized with a sodium hydroxide solution and stirred for 30 minutes at room temperature. The mixture is filtered over hyflo and the filtrate is acidified with acetic acid. The precipitated product is filtered off and dried, yielding 2.8 parts of 1-(4-hydroxyphenyl)-4-(methylsulfonyl)-piperazine; mp. 204.9° C.

EXAMPLE XLVII

To a stirred solution of 3.6 parts of N-(4-hydroxyphenyl)-N-methylacetamide in 100 parts of dimethylsulfoxide are added 0.7 parts of sodium hydride dispersions 78% and stirring is continued till foaming has ceased. Then there are added 8.4 parts of cis-2-(2,4-dichlorophenyl)-2-(1H-imidazol-1-ylmethyl)-1,3-dioxolan-4-ylmethyl methanesulfonate and the whole is stirred for 3 hours at 100° C. The reaction mixture is cooled and poured onto water. The product is extracted with dichloromethane. The extract is washed with a diluted sodium hydroxide solution, dried, filtered and evaporated. The residue is converted into the ethanedioate salt in 2-propanol. The salt is filtered off and crystallized from 2-propanol, yielding 9.2 parts of cis-N-{4-[2-(2,4-dichlorophenyl)-2-(1H-imidazol-1-ylmethyl)-1,3-dioxolan-4-ylmethoxy]phenyl}-N-methylacetamide ethanedioate (1:1); mp. 110° C.

EXAMPLE XLVIII

Following the procedure of Example IV and using equivalent amounts of the appropriate starting materials the following compounds are obtained in free base form or in the form of an acid addition salt after treating the free base with an appropriate acid:

| Ar | R4 | Base or Salt | Isomer | Mp. |
|---|---|---|---|---|
| 2,4-Cl2—C6H3 | CH3 | 2(COOH)2.C2H5OH | cis | 136.7° C. |

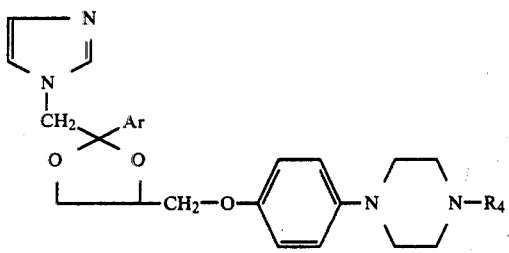

| Ar | R$_4$ | Base or Salt | Isomer | Mp. |
|---|---|---|---|---|
| 2,4-Cl$_2$—C$_6$H$_3$ | CH(CH$_3$)—CH$_2$—CH$_3$ | 3HCl.H$_2$O | cis | 193.6° C. |
| 2,4-Cl$_2$—C$_6$H$_3$ | CH$_2$—CH(CH$_3$)$_2$ | 3HCl.H$_2$O | cis | 179.8° C. |
| 2,4-Cl$_2$—C$_6$H$_3$ | CH(CH$_3$)$_2$ | 3HCl.CH$_3$—CHOH—CH$_3$ | cis | 192.8° C. |
| 2,4-Cl$_2$—C$_6$H$_3$ | (CH$_2$)$_3$CH$_3$ | 3HCl.H$_2$O | cis | 178.5° C. |
| 2,4-Cl$_2$—C$_6$H$_3$ | CH$_2$—CH$_2$—CH$_3$ | 2½ (COOH)$_2$ | cis | 171.1° C. |
| 2,4-Cl$_2$—C$_6$H$_3$ | CH$_2$—C$_6$H$_5$ | 3HCl.H$_2$O | cis | 212.8° C. |
| 3-CH$_3$—C$_6$H$_4$ | CO—CH$_3$ | (E)—HOOC—CH=CH—COOH | — | 162.7° C. |
| 2,4-Cl$_2$—C$_6$H$_3$ | C$_6$H$_5$ | base | cis | 209° C. |
| 3-Cl—C$_6$H$_4$ | CO—CH$_3$ | (COOH)$_2$ | cis | 190.9° C. |

EXAMPLE IL

Following the procedure of Example IV and using equivalent amounts of the appropriate starting materials the following compounds are still prepared:

cis-4-[2-(2,4-dichlorophenyl)-2-(1H-imidazol-1-ylmethyl)-1,3-dioxolan-4-ylmethoxy]-2-nitrobenzenamine; mp. 148.1° C.;

cis-4-[2-(2,4-dichlorophenyl)-2-(1H-imidazol-1-ylmethyl)-1,3-dioxolan-4-ylmethoxy]-N-ethylbenzenamine; mp. 143° C.; and cis-ethyl 4-{2-[2-(2,4-dichlorophenyl)-2-(1H-imidazol-1-ylmethyl)-1,3-dioxolan-4-ylmethoxy]-phenyl}-1-piperazinecarboxylate dihydrochloride; mp. 195.4° C.

EXAMPLE L

Following the procedure of Example III and using equivalent amounts of the appropriate starting materials the following compounds are prepared:

ethyl 4-{4-[2-(1H-imidazol-1-ylmethyl)-2-(4-methoxyphenyl)-1,3-dioxolan-4-ylmethoxy]phenyl}-1-piperazinecarboxylate (E)-2-butenedioate (2:1); mp. 159.9° C.;

1-acetyl-4-{4-[2-(1H-imidazol-1-ylmethyl)-2-(4-methoxyphenyl)-1,3-dioxolan-4-ylmethoxy]-phenyl}piperazine; mp. 171.4° C.;

cis-ethyl 4-{3-[2-(2,4-dichlorophenyl)-2-(1H-imidazol-1-ylmethyl)-1,3-dioxolan-4-ylmethoxy]-phenyl}-1-piperazinecarboxylate; mp. 119.5° C.; and cis-1-acetyl-4-{3-[2-(2,4-dichlorophenyl)-2-(1H-imidazol-1-ylmethyl)-1,3-dioxolan-4-ylmethoxy]-phenyl}piperazine dihydrobromide monohydrate; mp. 206.5° C.

EXAMPLE LI

Following the procedure of Example VII and using an equivalent amount of an appropriate N-(hydroxyphenyl)acetamide in place of the N-(4-hydroxyphenyl)-propanamide used therein, there are prepared:

cis-N-{2-[2-(2,4-dichlorophenyl)-2-(1H-imidazol-1-ylmethyl)-1,3-dioxolan-4-ylmethoxy]phenyl}acetamide nitrate; mp. 183.6° C.; and cis-N-{3-[2-(2,4-dichlorophenyl)-2-(1H-imidazol-1-ylmethyl)-1,3-dioxolan-4-ylmethoxy]phenyl}acetamide nitrate; mp. 170.5° C.

EXAMPLE LII

A mixture of 2.2 parts of N-(5-hydroxy-2-nitrophenyl)-acetamide, 4.2 parts of cis-[2-(2,4-dichlorophenyl)-2-(1H-imidazol-1-ylmethyl)-1,3-dioxolan-4-ylmethyl] methanesulfonate, 3 parts of potassium carbonate and 90 parts of N,N-dimethylformamide is stirred and heated overnight at 120° C. The reaction mixture is cooled and poured onto water The product is extracted twice with dichloromethane. The combined extracts are washed twice with a potassium carbonate solution, dried, filtered and evaporated. The residue is taken up in 80 parts of methanol and 2 parts of a sodium methanolate solution 30% are added. The whole is stirred and refluxed for 1 hour. The mixture is poured onto water and the layers are separated. The organic phase is dried, filtered and evaporated. The residue is converted into the hydrochloride salt in 2-propanol. The salt is filtered off and crystallized from ethanol, yielding 1.3 parts (25%) of cis-5-[2-(2,4-dichlorophenyl)-2-(1H-imidazol-1-ylmethyl)-1,3-dioxolan-4-ylmethoxy]-2-nitrobenzenamine monohydrochloride; mp. 242.9° C.

EXAMPLE LIII

Following the procedure of Example LII and using equivalent amounts of the appropriate starting materials, the following compound are prepared:

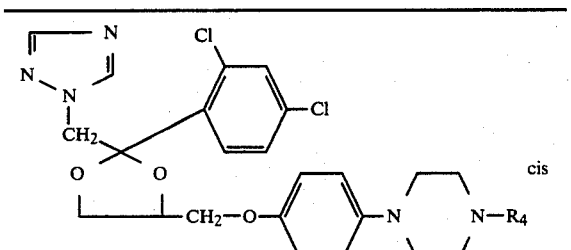

| R$_4$ | Base or Salt form | mp. |
|---|---|---|
| CH$_3$ | base | 126.1° C. |
| C$_2$H$_5$ | base | 122.2° C. |

-continued

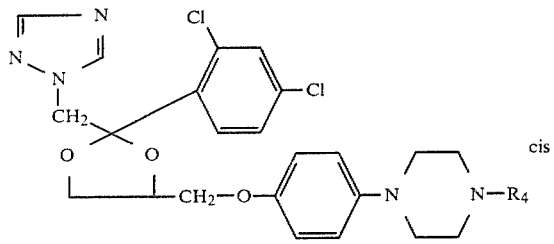

| R₄ | Base or Salt form | mp. |
| --- | --- | --- |
| CH₂—CH₂—CH₃ | base | 115.6° C. |
| CH(CH₃)₂ | base | 116.3° C. |
| (CH₂)₃—CH₃ | base | 111.4° C. |
| CH₂—CH(CH₃)₂ | base | 120.3° C. |
| CH(CH₃)—CH₂—CH₃ | base | 100.5° C. |
| CO—CH₃ | base | 176.4° C. |
| SO₂—CH₃ | base ½H₂O | 152.1° C. |
| CH₂—C₆H₅ | base | 107.1° C. |
| C₆H₅ | base | 134.1° C. |

EXAMPLE LIV

To a stirred and cooled (water-bath) mixture of 25 parts of cis-1-{4-[2-(2,4-dichlorophenyl)-2-(1H-imidazol-1-ylmethyl)-1,3-dioxolan-4-ylmethoxy]phenyl}piperazine, 27.7 parts of potassium carbonate and 375 parts of trichloromethane are added dropwise 5.7 parts of methyl carbonochloridate at a temperature between 20° and 23° C. Upon completion, stirring is continued for 2 hours. The reaction mixture is filtered over hyflo and the filtrate is evaporated. The residue is converted into the hydrochloride salt in 4-methyl-2-pentanone, a small amount of methanol and 2-propanol. The salt is filtered off and dried, yielding 23 parts (74.15%) of cis-methyl 4-{4-[2-(2,4-dichlorophenyl)-2-(1H-imidazol-1-ylmethyl)-1,3-dioxolan-4-ylmethoxy]phenyl}-1-piperazinecarboxylate dihydrochloride; mp. 192.9° C.

EXAMPLE LV

Following the procedure of Example LIV and using equivalent amounts of the appropriate starting materials the following compounds are prepared:
  cis-methyl 4-{4-[2-(2,4-dichlorophenyl)-2-(1H-1,2,4-triazol-1-ylmethyl)-1,3-dioxolan-4-ylmethoxy]phenyl}-1-piperazinecarboxylate; mp. 134.7° C.;
  cis-ethyl 4-{4-[2-(2,4-dichlorophenyl)-2-(1H-1,2,4-triazol-1-ylmethyl)-1,3-dioxolan-4-ylmethoxy]phenyl}-1-piperazinecarboxylate dihydrochloride; mp. 170.4° C.;
  cis-ethyl 4-{4-[2-(2,4-dichlorophenyl)-2-(1H-imidazol-1-ylmethyl)-1,3-dioxolan-4-ylmethoxy]phenyl}-1-piperazinecarboxylate dihydrochloride hemihydrate; mp. 178° C.; and
  cis-phenyl 4-{4-[2-(2,4-dichlorophenyl)-2-(1H-1,2,4-triazol-1-ylmethyl)-1,3-dioxolan-4-ylmethoxy]phenyl}-1-piperazinecarboxylate; mp. 112.4° C.

EXAMPLE LVI

A mixture of 1.56 parts of propanoic acid anhydride, 4.9 parts of cis-1-{4-[2-(2,4-dichlorophenyl)-2-(1H-1,2,4-triazol-1-ylmethyl)-1,3-dioxolan-4-ylmethoxy]phenyl}piperazine, 2 parts of potassium carbonate and 130 parts of dichloromethane is stirred for 2 hours at 10° C. Water is added and the layers are separated. The organic phase is washed with water, dried, filtered and evaporated. The residue is purified by column-chromatography over silica gel using a mixture of trichloromethane and methanol (97:3 by volume) as eluent. The pure fractions are collected and the eluent is evaporated. The residue is converted into the hydrochloride salt in 2,2'-oxybispropane and 2-propanol. The salt is filtered off and crystallized from a mixture of 2-propanol and 2,2'-oxybispropane, yielding 1.2 parts of cis-1-{4-[2-(2,4-dichlorophenyl)-2-(1H-1,2,4-triazol-1-ylmethyl)-1,3-dioxolan-4-ylmethoxy]phenyl}-4-(1-oxopropyl)piperazine dihydrochloride; mp. 180.9° C.

EXAMPLE LVII

Following the procedure of Example LVI and using an equivalent amount of butanoic acid anhydride in place of the propanoic acid anhydride used therein there is prepared:
  cis-1-{4-[2-(2,4-dichlorophenyl)-2-(1H-1,2,4-triazol-1-ylmethyl)-1,3-dioxolan-4-ylmethoxy]phenyl}-4-(1-oxobutyl)piperazine dihydrochloride; mp. 177.7° C.

EXAMPLE LVIII

A mixture of 1.34 parts of ethyl 2-chloroacetate, 5 parts of cis-1-{4-[2-(2,4-dichlorophenyl)-2-(1H-imidazol-1-ylmethyl)-1,3-dioxolan-4-ylmethoxy]phenyl}piperazine, 2.75 parts of potassium carbonate and 45 parts of N,N-dimethylformamide is stirred and heated for 1 hour at 60° C. The reaction mixture is poured onto ice-water. The product is extracted with dichloromethane. The extract is washed with water, dried, filtered and evaporated. The oily residue is purified by column-chromatography over silica gel using a mixture of methylbenzene and ethanol (90:10 by volume) as eluent. The pure fractions are collected and the eluent is evaporated. The oily residue is crystallized from 4-methyl-2-pentanone. The product is filtered off and dried, yielding 2 parts of cis-ethyl 4-{4-[2-(2,4-dichlorophenyl)-2-(1H-imidazol-1-ylmethyl)-1,3-dioxolan-4-ylmethoxy]-phenyl}-1-piperazineacetate; mp. 130.7° C.

EXAMPLE LIX

A mixture of 1 part of 2-chloroacetamide, 5 parts of cis-1-{4-[2-(2,4-dichlorophenyl)-2-(1H-imidazol-1-ylmethyl)-1,3-dioxolan-4-ylmethoxy]phenyl}piperazine, 2.76 parts of potassium carbonate and 50 parts of dimethylsulfoxide is stirred for 60 hours at room temperature. The reaction mixture is poured onto water and the product is extracted with dichloromethane. The extract is washed with water, dried, filtered and evaporated. The solid residue is purified by column-chromatography over silica gel using a mixture of trichloromethane and methanol (95:5 by volume) as eluent. The pure fractions are collected and the eluent is evaporated, yielding 1.5 parts of cis-4-{4-[2-(2,4-dichlorophenyl)-2-(1H-imidazol-1-ylmethyl)-1,3-dioxolan-4-ylmethoxy]phenyl}-1-piperazineacetamide; mp. 150.2° C.

EXAMPLE LX

To a stirred solution of 5 parts of ethanamine in 55 parts of 1,2-ethanediol are added 4.5 parts of cis-ethyl 4-{4-[2-(2,4-dichlorophenyl)-2-(1H-imidazol-1-ylmethyl)-1,3-dioxolan-4-ylmethoxy]phenyl}-1-piperazineacetate and the whole is stirred first for 5 hours at 40° C. and further for 48 hours at room temperature. The reaction mixture is poured onto water and the product is extracted with dichloromethane. The extract is dried, filtered and evaporated. The oily residue is crystallized from a mixture of ethyl acetate and 2,2'-oxybispropane. The product is filtered off and dried, yielding 3 parts of cis-4-{4-[2-(2,4-dichlorophenyl)-2-(1H-imidazol-1-ylmethyl)-1,3-dioxolan-4-ylmethoxy]phenyl}-N-ethyl-1-piperazineacetamide; mp. 117.2° C.

EXAMPLE LXI

Following the procedure of Example LX and using an equivalent amount of methanamine in place of the ethanamine used therein there is prepared:
cis-4-{4-[2-(2,4-dichlorophenyl)-2-(1-imidazol-1-ylmethyl)-1,3-dioxolan-4-ylmethoxy]phenyl}-N-methyl-1-piperazineacetamide trihydrochloride. monohydrate; mp. 212.2° C.

EXAMPLE LXII

A mixture of 20.7 parts of cis-N-{4-[2-(2,4-dichlorophenyl)-2-(1-imidazol-1-ylmethyl)-1,3-dioxolan-4-ylmethoxy]phenyl}-N-methylacetamide ethanedioate (1:1), 15 parts of potassium hydroxide and 160 parts of 2-propanol is stirred and refluxed overnight. The reaction mixture is cooled and poured onto water. The product is extracted with dichloromethane. The extract is washed with water, dried, filtered and evaporated. The residue is converted into the ethanedioate salt in ethanol. The salt is filtered off. The free base is liberated in the conventional manner and crystallized from 1,1'-oxybisethane, yielding 9 parts (57%) of cis-4-[2-(2,4-dichlorophenyl)-2-(1H-imidazol-1-ylmethyl)-1,3-dioxolan-4-ylmethoxy]-N-methylbenzenamine; mp. 118.4° C.

EXAMPLE LXIII

A mixture of 53.7 parts of cis-1-acetyl-4-{4-[2-(2,4-dichlorophenyl)-2-(1H-1,2,4-triazol-1-ylmethyl)-1,3-dioxolan-4-ylmethoxy]phenyl}piperazine, 4.9 parts of sodium hydroxide and 800 parts of 1-butanol is stirred and refluxed overnight. The reaction mixture is cooled and poured onto water. The product is extracted with benzene. The extract is washed twice with water, dried, filtered and evaporated. The residue is purified by column-chromatography over silica gel using a mixture of trichloromethane and methanol (95:5 by volume), saturated with ammonia, as eluent. The pure fractions are collected and the eluent is evaporated. The residue is crystallized from 2,2'-oxybispropane. The product is filtered off and dried, yielding 11.7 parts of cis-1-{4-[2-(2,4-dichlorophenyl)-2-(1H-1,2,4-triazol-1-ylmethyl)-1,3-dioxolan-4-ylmethoxy]-phenyl}piperazine; mp. 130.6° C.

EXAMPLE LXIV

A mixture of 60 parts of formic acid and 6 parts of cis-1-{4-[2-(2,4-dichlorophenyl)-2-(1H-1,2,4-triazol-1-ylmethyl)-1,3-dioxolan-4-ylmethoxy]phenyl}piperazine is stirred and refluxed overnight. The reaction mixture is evaporated and the residue is dissolved in water. The solution is alkalized with ammonium hydroxide and the product is extracted twice with dichloromethane. The combined extracts are washed twice with water, dried, filtered and evaporated. The residue is purified by column-chromatography over silica gel using a mixture of trichloromethane, hexane and methanol (45:45:10 by volume) as eluent. The pure fractions are collected and the eluent is evaporated. The residue is crystallized from 4-methyl-2-pentanone. The product is filtered off and dried, yielding 2.5 parts of cis-4-{4-[2-(2,4-dichlorophenyl)-2-(1H-1,2,4-triazol-1-ylmethyl)-1,3-dioxolan-4-ylmethoxy]phenyl}-1-piperazinecarboxaldehyde; mp. 137.3° C.

EXAMPLE LXV

A mixture of 2.3 parts of benzoyl chloride, 7.35 parts of cis-1-{4-[2-(2,4-dichlorophenyl)-2-(1H-1,2,4-triazol-1-ylmethyl)-1,3-dioxolan-4-ylmethoxy]phenyl}piperazine, 3 parts of potassium carbonate and 130 parts of dichloromethane is stirred for 2 hours at room temperature. The reaction mixture is washed with water, dried, filtered and evaporated. The residue is purified by column-chromatography over silica gel using a mixture of trichloromethane and methanol (95:5 by volume) as eluent. The pure fractions are collected and the eluent is evaporated. The residue is crystallized from 2,2'-oxybispropane. The product is filtered off and dried, yielding 1.8 parts of cis-1-benzoyl-4-{4-[2-(2,4-dichlorophenyl)-2-(1H-1,2,4-triazol-1-ylmethyl)-1,3-dioxolan-4-ylmethoxy]phenyl}piperazine; mp. 140.3° C.

EXAMPLE LXVI

A mixture of 1.3 parts of methanesulfonyl chloride, 4.9 parts of cis-1-{4-[2-(2,4-dichlorophenyl)-2-(1H-imidazol-1-ylmethyl)-1,3-dioxolan-4-ylmethoxy]phenyl}piperazine, 3 parts of potassium carbonate and 150 parts of trichloromethane is stirred for 3 hours at room temperature. Then there are added 100 parts of water and stirring is continued for 1 hour at room temperature. The organic phase is separated, dried, filtered and evaporated. The residue is triturated in a mixture of 4-methyl-2-pentanone and five drops of water. Upon the addition of 2,2'-oxybispropane, the product is precipitated. It is filtered off and crystallized from 4-methyl-2-pentanone, yielding 5 parts of cis-1-{4-[2-(2,4-dichlorophenyl)-2-(1H-imidazol-1-ylmethyl)-1,3-dioxolan-4-ylmethoxy]phenyl}-4-(methylsulfonyl)piperazine monohydrate; mp. 113° C.

EXAMPLE LXVII

Following the produce of Example LXVI and using equivalent amounts of the appropriate starting materials there are prepared:
cis-1-{4-[2-(2,4-dichlorophenyl)-2-(1H-imidazol-1-ylmethyl)-1,3-dioxolan-4-ylmethoxy]phenyl}-4-(phenylmethylsulfonyl)piperazine; mp. 188.2° C.; and
cis-1-{4-[2-(2,4-dichlorophenyl)-2-(1H-1,2,4-triazol-1-ylmethyl)-1,3-dioxolan-4-ylmethoxy]phenyl}-4-(phenylmethylsulfonyl)piperazine monohydrate; mp. 135.1° C.

EXAMPLE LXVIII

During 1 hour, gaseous oxirane is bubbled through a stirred mixture of 5 parts of cis-1-{4-[2-(2,4-dichlorophenyl)-2-(1H-imidazol-1-ylmethyl)-1,3-dioxolan-4-ylmethoxy]phenyl}piperazine and 80 parts of methanol at reflux temperature. The reaction mixture is evaporated. The residue is purified by column-chromatography over silica gel using a mixture of trichloromethane and methanol (95:5 by volume) as eluent. The pure fractions are collected and the eluent is evaporated. The oily residue is crystallized from a mixture of benzene and petroleumether. The product is filtered off and dired, yielding 2 parts of cis-4-{4-[2-(2,4-dichlorophenyl)-2-(1H-imidazol-1-ylmethyl)-1,3-dioxolan-4-ylmethoxy]phenyl}-1-piperazineethanol; mp. 146.4° C.

A mixture of 5.3 parts of cis-4-{4-[2-(2,4-dichlorophenyl)-2-(1H-imidazol-1-ylmethyl)-1,3-dioxolan-4-ylmethoxy]phenyl}-1-piperazineethanol, 50 parts of dimethylsulfoxide and 45 parts of benzene is stirred till all solid enters solution. Then there are added 0.622 parts of sodium hydride dispersion 76% and stirring at room temperature is continued till gas-evolution has ceased. 2.2 Parts of bromoethane are added and the whole is stirred overnight at room temperature. Another 2 parts of bromoethane are added in two separate portions, each time with a 2 hours-time interval. The reaction mixture is poured onto ice-water and the product is extracted with dichloromethane. The extract is washed with water, dried, filtered and evaporated. The oily residue is purified by column-chromatography over silica gel using a mixture of trichloromethane and methanol (95:5 by volume) as eluent. The pure fractions are collected and the eluent is evaporated. The oily residue is crystallized from 4-methyl-2-pentanone. The product is filtered off and dried, yielding 2.7 parts of cis-1-{4-[2-(2,4-dichlorophenyl)-2-(1H-imidazol-1-ylmethyl)-1,3-dioxolan-4-ylmethoxy]phenyl}-4-(2-ethoxyethyl)piperazine; mp. 140°–145.4° C.

EXAMPLE LXIX

A mixture of 5 parts of cis-1-acetyl-4-{4-[2-(2,4-dichlorophenyl)-2-(1H-imidazol-1-ylmethyl)-1,3-dioxolan-4-ylmethoxy]-phenyl}piperazine, 1 part of lithium aluminium hydride and 90 parts of tetrahydrofuran is stirred for one week at room temperature. The reaction mixture is decomposed by the successive additions of 1 part of water, 1.50 parts of a sodium hydroxide solution 50% and 3 parts of water. The precipitate is filtered off and the filtrate is evaporated. The residue is converted into the ethanedioate salt in ethanol. The salt is filtered off and dried, yielding 3.7 parts (56%) of cis-1-{4-[2-(2,4-dichlorophenyl)-2-(1H-imidazol-1-ylmethyl)-1,3-dioxolan-4-ylmethoxy]phenyl}-4-ethylpiperazine ethanedioate; mp. 169.7° C.

EXAMPLE LXX

A mixture of 60 parts of cis-1-acetyl-4-{4-[2-(2,4-dichlorophenyl)-2-(1H-imidazol-1-ylmethyl)-1,3-dioxolan-4-ylmethoxy]phenyl}piperazine and 400 parts of 4-methyl-2-pentanone is heated to reflux and treated with activated charcoal. The latter is filtered off and the filtrate is cooaled to about 30° C. Then there are added slowly 29 parts of 2-propanol, saturated with gaseous hydrogen chloride and upon stirring, the formed hydrochloride salt is allowed to crystallized (3 hours). It is filtered off and recrystallized twice from 2-propanol, yielding 38 parts of cis-1-acetyl-4-{4-[2-(2,4-dichlorophenyl)-2-(1H-imidazol-1-ylmethyl)-1,3-dioxolan-4-ylmethoxy]phenyl}piperazine dihydrochloride; mp. 219.3° C.

EXAMPLE LXXI

Following the procedure of Example XXXVI and using equivalent amounts of the appropriate starting materials the following methanesulfonates are still prepared:

[2-(4-chlorophenyl)-2-(1H-imidazol-1-ylmethyl)-1,3-dioxolan-4-ylmethyl] methanesulfonate;
[2-(4-bromophenyl)-2-(1H-imidazol-1-ylmethyl)-1,3-dioxolan-4-ylmethyl] methanesulfonate;
[2-(4-fluorophenyl)-2-(1H-imidazol-1-ylmethyl)-1,3-dioxolan-4-ylmethyl] methanesulfonate;
[2-(2,6-dichlorophenyl)-2-(1H-imidazol-1-ylmethyl)-1,3-dioxolan-4-ylmethyl] methanesulfonate;
[2-(2-(1H-imidazol-1-ylmethyl)-2-(4-methylphenyl)-1,3-dioxolan-4-ylmethyl] methanesulfonate; and
[2-(2-(1H-imidazol-1-ylmethyl)-2-(4-chloro-2-methylphenyl)-1,3-dioxolan-4-ylmethyl] methanesulfonate.

EXAMPLE LXXII

Following the procedure of Example IV and using equivalent amounts of the appropriate starting materials, the following compounds of formula I are still prepared:

4-[2-(3-chlorophenyl)-2-(1H-imidazol-1-ylmethyl)-1,3-dioxolan-4-ylmethoxy]-N-ethylbenzenamine;
4-[2-(4-bromophenyl)-2-(1H-imidazol-1-ylmethyl)-1,3-dioxolan-4-ylmethoxy]-N-ethylbenzenamine;
N-ethyl-4-[2-(1H-imidazol-1-ylmethyl)-2-(3-methylphenyl)-1,3-dioxolan-4-ylmethoxy]benzenamine;
N-ethyl-4-[2-(1H-imidazol-1-ylmethyl)-2-(4-methoxyphenyl)-1,3-dioxolan-4-ylmethoxy]benzenamine;
4-[2-(2,4-dichlorophenyl)-2-(1H-1,2,4-triazol-1-ylmethyl)-1,3-dioxolan-4-ylmethoxy]-N-ethylbenzenamine;
N-{4-[2-(3-chlorophenyl)-2-(1H-imidazol-1-ylmethyl)-1,3-dioxolan-4-ylmethoxy]phenyl}acetamide.
N-{4-[2-(4-bromophenyl)-2-(1H-imidazol-1-ylmethyl)-1,3-dioxolan-4-ylmethoxy]phenyl}benzamide
ethyl{4-[2-(1H-imidazol-1-ylmethyl)-2-(3-methylphenyl)-1,3-dioxolan-4-ylmethoxy]phenyl}carbamate;
N-{4-[2-(1H-imidazol-1-ylmethyl)-2-(4-methoxyphenyl)-1,3-dioxolan-4-ylmethoxy]phenyl}-4-fluorobenzamide;
N-{4-[2-(2,4-dichlorophenyl)-2-(1H-1,2,4-triazol-1-ylmethyl)-1,3 dioxolan-4-ylmethoxy]phenyl}acetamide;
1-{2-(3-chlorophenyl)-4-[4-(1-pyrrolidinyl)phenoxymethyl]-1,3-dioxolan-2-ylmethyl}-1H-imidazole;
1-{2-(4-bromophenyl)-4-[4-(1-piperidinyl)phenoxymethyl]-1,3-dioxolan-2-ylmethyl}-1H-imidazole;
1-{2-(3-methylphenyl)-4-[4-(1-pyrrolidinyl)phenoxymethyl]-1,3-dioxolan-2-ylmethyl}-1H-imidazole;
1-{2-(4-methoxyphenyl)-4-[4-(1-piperidinyl)phenoxymethyl]-1,3-dioxolan-2-ylmethyl}-1H-imidazole;
1-{2-(2,4-dichlorophenyl)-4-[4-(1-pyrrolidinyl)phenoxymethyl]-1,3-dioxolan-2-ylmethyl}-1H-1,2,4-triazole;
1-{2-(2,4-dichlorophenyl)-4-[4-(1-piperidinyl)phenoxymethyl]-1,3-dioxolan-2-ylmethyl}-1H-1,2,4-triazole;
4-{4-[2-(3-chlorophenyl)-2-(1H-imidazol-1-ylmethyl)-1,3-dioxolan-4-ylmethoxy]phenyl}morpholine;
4-{4-[2-(1H-imidazol-1-ylmethyl)-2-(3-methylphenyl)-1,3-dioxolan-4-ylmethoxy]phenyl}morpholine;
4-{4-[2-(1H-imidazol-1-ylmethyl)-2-(4-methoxyphenyl)-1,3-dioxolan-4-ylmethoxy]phenyl}morpholine; and
4-{4-[2-(2,4-dichlorophenyl)-2-(1H-1,2,4-triazol-1-ylmethyl)-1,3-dioxolan-4-ylmethoxy]phenyl}morpholine.

We claim:

1. A chemical compound selected from the group consisting of an azole derivative having the formula:

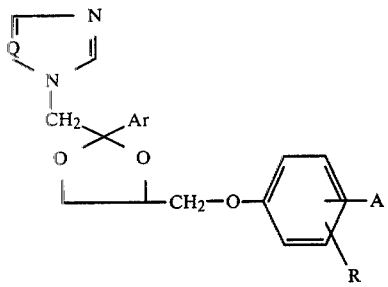

and the pharmaceutically acceptable acid addition salts and stereochemically isomeric forms thereof, wherein:

Q is N;

Ar is a member selected from the group consisting of phenyl and substituted phenyl, said substituted phenyl being phenyl having from 1 to 3 substituents independently selected from the group consisting of halo, lower alkyl and lower alkyloxy;

A is a radical of the formula

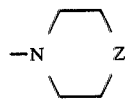

wherein Z is a member selected from the group consisting of a direct bond, $CH_2$, O and $N-R_4$, wherein $R_4$ is selected from the group consisting of hydrogen, lower alkyl, hydroxy(lower alkyl), (lower alkyloxy)lower alkyl, lower alkanoyl, lower alkylsulfonyl, phenylmethylsulfonyl, lower alkyloxycarbonyl, lower alkyloxycarbonylmethyl, phenoxycarbonyl, aminocarbonyl, mono- and di(-lower alkyl)aminocarbonyl, aminocarbonylmethyl, (lower alkyl)aminocarbonylmethyl, (lower alkyl) aminothioxomethyl, (lower alkylthio)thioxomethyl, phenyl, phenylmethyl, benzoyl and substituted benzoyl, said substituted benzoyl being benzoyl having from 1 to 2 substituents independently selected from the group consisting of halo, lower alkyl and lower alkyloxy; and R is hydrogen.

2. A chemical compound selected from the group consisting of cis-methyl 4-{4-[2-(2,4-dichlorophenyl)-2-(1H-1,2,4-triazol-1-ylmethyl)-1,3-dioxolan-4-ylmethoxy]phenyl}-1-piperazine-carboxylate and the pharmaceutically acceptable acid addition salts and stereochemically isomeric forms thereof.

3. A chemical compound selected from the group consisting of cis-1-{4-[2-(2,4-dichlorophenyl)-2-(1H-1,2,4-triazol-1-ylmethyl)-1,3-dioxolan-4-ylmethoxy]-phenyl}piperazine and the pharmaceutically acceptable acid addition salts and stereochemically isomeric forms thereof.

4. A chemical compound selected from the group consisting of cis-4-{4-[2-(2,4-dichlorophenyl)-2-(1H-1,2,4-triazol-1-ylmethyl)-1,3-dioxolan-4-ylmethoxy]-phenyl}-1-piperazinecarboxaldehyde and the pharmaceutically acceptable acid addition salts and stereochemically isomeric forms thereof.

5. A chemical compound selected from the group consisting of 4-{4-[2-(2,4-dichlorophenyl)-2-(1H-1,2,4-triazol-1-ylmethyl)-1,3-dioxolan-4-ylmethoxy]phenyl}-morpholine and the pharmaceutically acceptable acid addition salts and stereochemically isomeric forms thereof.

6. A chemical compound selected from the group consisting of cis-1-{4-[2-(2,4-dichlorophenyl)-2-(1H-1,2,4-triazol-1-ylmethyl)-1,3-dioxolan-4-ylmethoxy]-phenyl}-4-(1-methylethyl)piperazine and the pharmaceutically acceptable acid addition salts and stereochemically isomeric forms thereof.

7. A composition for combatting a microorganism selected from the group consisting of fungus and bacterium comprising an inert carrier material and as an active ingredient an effective amount of a compound selected from the group consisting of an azole derivative having the formula:

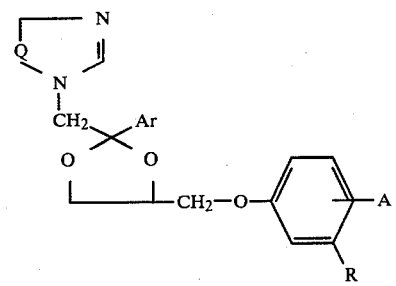

and the pharmaceutically acceptable acid addition salts and stereochemically isomeric forms thereof, wherein:

Q is N;

Ar is a member selected from the group consisting of phenyl and substituted phenyl, said substituted phenyl being phenyl having from 1 to 3 substituents independently selected from the group consisting of halo, lower alkyl and lower alkyloxy;

A is a radical of the formula

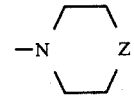

wherein Z is a member selected from the group consisting of a direct bond, $CH_2$, O and $N-R_4$ wherein $R_4$ is selected from the group consisting of hydrogen, lower alkyl, hydroxy(lower alkyl), (lower alkyloxy)lower alkyl, lower alkanoyl, lower alkylsulfonyl, phenylmethylsulfonyl, lower alkyloxycarbonyl, lower alkyloxycarbonylmethyl, phenoxycarbonyl, aminocarbonyl, mono- and di(-lower alkyl)aminocarbonyl, aminocarbonylmethyl, (lower alkyl)aminocarbonylmethyl, (lower alkyl) aminothioxomethyl, (lower alkylthio) thioxomethyl, phenyl, phenylmethyl, benzoyl and substituted benzoyl, said substituted benzoyl being benzoyl having from 1 to 2 substituents independently selected from the group consisting of halo, lower alkyl and lower alkyloxy; and R is hydrogen.

* * * * *

UNITED STATES PATENT AND TRADEMARK OFFICE

CERTIFICATE EXTENDING PATENT TERM UNDER 35 U.S.C. 156

Patent No.    : 4,358,449

Dated         : November 9, 1982

Inventor(s)   : Jan Heeres et al

Patent Owner  : Janssen Pharmaceutica N.V.

This is to certify that there has been presented to the

COMMISSIONER OF PATENTS AND TRADEMARKS an application under 35 U.S.C. 156 for an extension of the patent term. Since it appears that the requirements of law have been met, this certificate extends the term of the patent for the period of

2 YEARS with all rights pertaining thereto as provided by 35 USC 156(b).

I have caused the seal of the Patent and Trademark Office to be affixed this Twenty-Eighth day of December 1988.

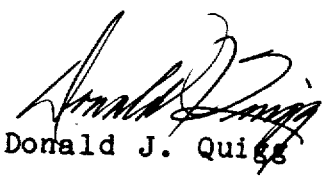

Donald J. Quigg

Assistant Secretary and Commissioner of Patents and Trademarks